United States Patent
Sandhu et al.

(10) Patent No.: US 9,320,573 B2
(45) Date of Patent: *Apr. 26, 2016

(54) MULTI-USER TOUCH-BASED CONTROL OF A REMOTE CATHETER GUIDANCE SYSTEM (RCGS)

(71) Applicant: St. Jude Medical, Atrial Fibrillation Division, Inc., St. Paul, MN (US)

(72) Inventors: Kulbir S. Sandhu, Fremont, CA (US); Huaicai Mo, Milpitas, CA (US); Venkata Adusumilli, Santa Clara, CA (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/583,870

(22) Filed: Dec. 29, 2014

(65) Prior Publication Data

US 2015/0182297 A1 Jul. 2, 2015

Related U.S. Application Data

(63) Continuation of application No. 13/334,470, filed on Dec. 22, 2011, now Pat. No. 8,920,368.

(51) Int. Cl.
| | |
|---|---|
| *A61B 19/00* | (2006.01) |
| *A61B 6/12* | (2006.01) |
| *A61B 17/00* | (2006.01) |
| *A61B 18/14* | (2006.01) |

(52) U.S. Cl.
CPC . *A61B 19/56* (2013.01); *A61B 6/12* (2013.01); *A61B 17/00234* (2013.01); *A61B 19/2203* (2013.01); *A61B 19/50* (2013.01); *A61B 19/5244* (2013.01); *A61B 18/1492* (2013.01); *A61B 2017/00044* (2013.01); *A61B 2017/00207* (2013.01); *A61B 2017/00243* (2013.01); *A61B 2017/00292* (2013.01); *A61B 2019/2211* (2013.01); *A61B 2019/505* (2013.01); *A61B 2019/507* (2013.01); *A61B 2019/524* (2013.01); *A61B 2019/5236* (2013.01); *A61B 2019/5263* (2013.01); *A61B 2019/5274* (2013.01); *A61B 2019/568* (2013.01)

(58) Field of Classification Search
CPC ...................... A61M 25/0147; A61M 25/0136; A61M 25/0144; A61M 2025/015; A61M 2025/0161; A61B 19/56; A61B 6/12; A61B 17/00234; A61B 19/2203; A61B 19/50; A61B 19/5244; A61B 2017/00044; A61B 2017/00207; A61B 2017/00243; A61B 2017/00292; A61B 2019/2211; A61B 2019/505; A61B 2019/507; A61B 2019/5236; A61B 2019/524; A61B 2019/5263; A61B 2019/5274; A61B 2019/568
USPC .......................... 604/95.01, 65–67, 131, 151; 128/DIG. 12, DIG. 13

See application file for complete search history.

(56) References Cited

U.S. PATENT DOCUMENTS

| | | | |
|---|---|---|---|
| 5,366,896 | A | 11/1994 | Margrey et al. |
| 6,233,476 | B1 | 5/2001 | Strommer |

(Continued)

FOREIGN PATENT DOCUMENTS

| | | |
|---|---|---|
| WO | 2009/120982 | 10/2009 |
| WO | 2011/123669 | 10/2011 |

*Primary Examiner* — Manuel Mendez
(74) *Attorney, Agent, or Firm* — Dykema Gossett PLLC

(57) ABSTRACT

A control system for a medical remote catheter guidance system includes an ECU, a computer-readable memory coupled to the ECU, and user interface (UI) logic stored in the memory configured to be executed by the ECU. The user interface logic receives input from a touch screen display with respect to a view of an anatomical model, associates a user type with the input, and interprets the input according to the associated user type and input. The user interface logic may be further configured to receive simultaneous inputs from at least two different users and to associate different user types with each of said simultaneous inputs. The user interface logic may associate each input with a user type according to a location of the input on the touch screen display.

18 Claims, 15 Drawing Sheets

(56) References Cited

U.S. PATENT DOCUMENTS

| | | |
|---|---|---|
| 6,964,867 B2 | 11/2005 | Downs |
| 7,197,354 B2 | 3/2007 | Sobe |
| 7,263,397 B2 | 8/2007 | Hauck |
| 7,386,339 B2 | 6/2008 | Strommer |
| 8,920,368 B2 * | 12/2014 | Sandhu et al. ............. 604/95.01 |
| 2008/0249536 A1 | 10/2008 | Stahler |
| 2009/0012533 A1 | 1/2009 | Barbagli |
| 2009/0247942 A1 | 10/2009 | Kirschenman |
| 2009/0247943 A1 | 10/2009 | Kirschenman |
| 2009/0247944 A1 | 10/2009 | Kirschenman |
| 2009/0247993 A1 | 10/2009 | Kirschenman |
| 2009/0248042 A1 | 10/2009 | Kirschenman |
| 2010/0256558 A1 | 10/2010 | Olson et al. |
| 2011/0015569 A1 | 1/2011 | Kirschenman |

\* cited by examiner

MULTI-USER TOUCH-BASED CONTROL OF A REMOTE CATHETER GUIDANCE SYSTEM (RCGS)

CROSS-REFERENCE TO RELATED APPLICATIONS

The present application is a continuation of U.S. application Ser. No. 13/334,470, filed 22 Dec. 2011, now pending, which is hereby incorporated by reference as though fully set forth herein.

BACKGROUND OF THE INVENTION a. Field of the Invention

The present disclosure relates generally to a remote catheter guidance system (RCGS) for a medical device, and more particularly to a multi-user touch-based input interface for an RCGS.

b. Background Art

Electrophysiology (EP) catheters are used in a variety of diagnostic and/or therapeutic medical procedures to correct conditions such as atrial arrhythmia, including for example, ectopic atrial tachycardia, atrial fibrillation, and atrial flutter. Arrhythmia can create a variety of dangerous conditions including irregular heart rates, loss of synchronous atrioventricular contractions and stasis of blood flow which can lead to a variety of ailments.

In a typical EP procedure, a physician manipulates a catheter through a patient's vasculature to, for example, a patient's heart. The catheter typically carries one or more electrodes that may be used for mapping, ablation, diagnosis, and the like. Once at the target tissue site, the physician commences diagnostic and/or therapeutic procedures, for example, ablative procedures such as radio frequency (RF), microwave, cryogenic, laser, chemical, acoustic/ultrasound or high-intensity focused ultrasound (HIFU) ablation, to name a few different sources of ablation energy. The resulting lesion, if properly located and sufficiently contiguous with other lesions, disrupts undesirable electrical pathways and thereby limits or prevents stray electrical signals that can lead to arrhythmias. Such procedures require precise control of the catheter during navigation to and delivery of therapy to the target tissue site, which can be a function of a user's skill level.

Robotic catheter systems are known to facilitate such precise control. Robotic catheter systems generally carry out (as a mechanical surrogate) input commands of a clinician or other end-user to deploy, navigate and manipulate a catheter and/or an introducer or sheath for a catheter or other elongate medical instrument, for example, a robotic catheter system described, depicted, and/or claimed in U.S. application Ser. No. 12/347,811 entitled "ROBOTIC CATHETER SYSTEM," owned by the common assignee of the present disclosure and hereby incorporated by reference in its entirety as though fully set forth herein. Such robotic catheter systems include a variety of actuation mechanisms, such as electric motors, for controlling translation and deflection of the catheter and associated sheath. A variety of input devices are generally used, such as a mouse, keyboard, joystick, and touch screen. But known input mechanisms and interfaces for robotic catheter systems limit the types of input actions available to a user and the speed and precision with which a user can enter those input actions.

There is therefore a need for improved systems and methods that enhance clinician control while reducing the time required for a robotic procedure to thereby minimize or eliminate one or more problems noted above.

BRIEF SUMMARY OF THE INVENTION

It is desirable for a control system for user-guided robotic manipulation of a medical device to include input apparatus and user interfaces that enable intuitive user input while safely improving the speed and precision of user input. Such a control system comprises an electronic control unit (ECU), a computer-readable memory coupled to the ECU, and user interface (UI) logic stored in the memory configured to be executed by the ECU. The user interface logic may be configured to receive input from a touch screen display with respect to a view of an anatomical model, and interpret the input. The system further comprises control logic stored in the memory configured to be executed by the ECU, the control logic configured to produce an actuation control signal based at least in part on the interpretation of the UI logic and the input to control the medical device. In an embodiment, the control logic is configured to produce an actuation control signal to control the actuation of a manipulator assembly.

The user interface logic may be further configured to associate a user type with the input and to interpret the input according to the user type associated with the input. The input may be associated with a user type according to a location of the input on the touch screen display. In a further embodiment, the user interface logic may be configured to receive simultaneous inputs from at least two different users and to associate user types with each of said simultaneous inputs. The user interface logic may associate each input with a user type according to a location of the input on the touch screen display. The user interface logic may also be configured to receive inputs from at least two different points on the touch screen display, and may further be configured to receive the input from at least two different points simultaneously.

The user interface logic may receive said input as one or more gestures or as raw touch input data. The raw touch input data may include a location of the input and a pressure of the input or a location of the input and a speed of the input.

In another embodiment, the control system comprises the ECU, memory, a set of user types stored in the memory, and UI logic. The UI logic is configured to arrange a view of an anatomical model and a representation of the medical device in a graphical interface on a touch screen display, receive multiple touch-based inputs from the display with respect to the view of the anatomical model and the representation of the medical device, associate a user type from the set of user types with each of the multiple touch-based inputs, and determine whether the medical device should be moved and whether the anatomical model should be updated according to each of the associated touch based inputs user types. In an embodiment, the view of the anatomical model and the representation of the medical device may be arranged in a first interface portion, and a second view of the anatomical model may be arranged in a second interface portion, where the second view is at a different angle from the first view.

The user interface logic may associate an area of the touch screen display with one user type in the set of user types. Each user type in the set of user types may be associated with one or more permissions. The permissions may include permission to move the medical device and permission to manipulate the anatomical model.

In yet another embodiment, the control system comprises the ECU, memory, and logic. The logic is configured to provide a user login interface on a touch screen display, obtain login information from a user via the user login interface, verify the login information, define an input area for the user, and receive touch-based input from the input area. The logic is further configured to produce an actuation control signal based at least in part on the touch-based input from the input area to control actuation of a manipulator assembly so as to move the medical device.

The logic may be further configured to dissociate the area of the touch screen with the particular user type according to a dissociation event. The dissociation event may be selected from the group consisting of a logout input from said user, the passage of a pre-determined amount of time without an input in the area, and the passage of a pre-determined amount of time after the logic associates the area with the user type.

The foregoing and other aspects, features, details, utilities, and advantages of the present disclosure will be apparent from reading the following description and claims, and from reviewing the accompanying drawings.

DETAILED DESCRIPTION OF THE INVENTION

Before proceeding to a detailed description of the proximity/contact sensor interface for a robotic catheter system, a brief overview (for context) of an exemplary remote catheter guidance system (RCGS) for manipulating a medical device will first be described. The description of the RCGS will detail how several electric motors can be used to control the translation, distal bending and virtual rotation of a catheter and surrounding sheath. After the description of the RCGS, the present specification will then provide a description of operating the RCGS with a touch-sensitive input device such as, for example, a multi-user touch screen display.

Figure 1:
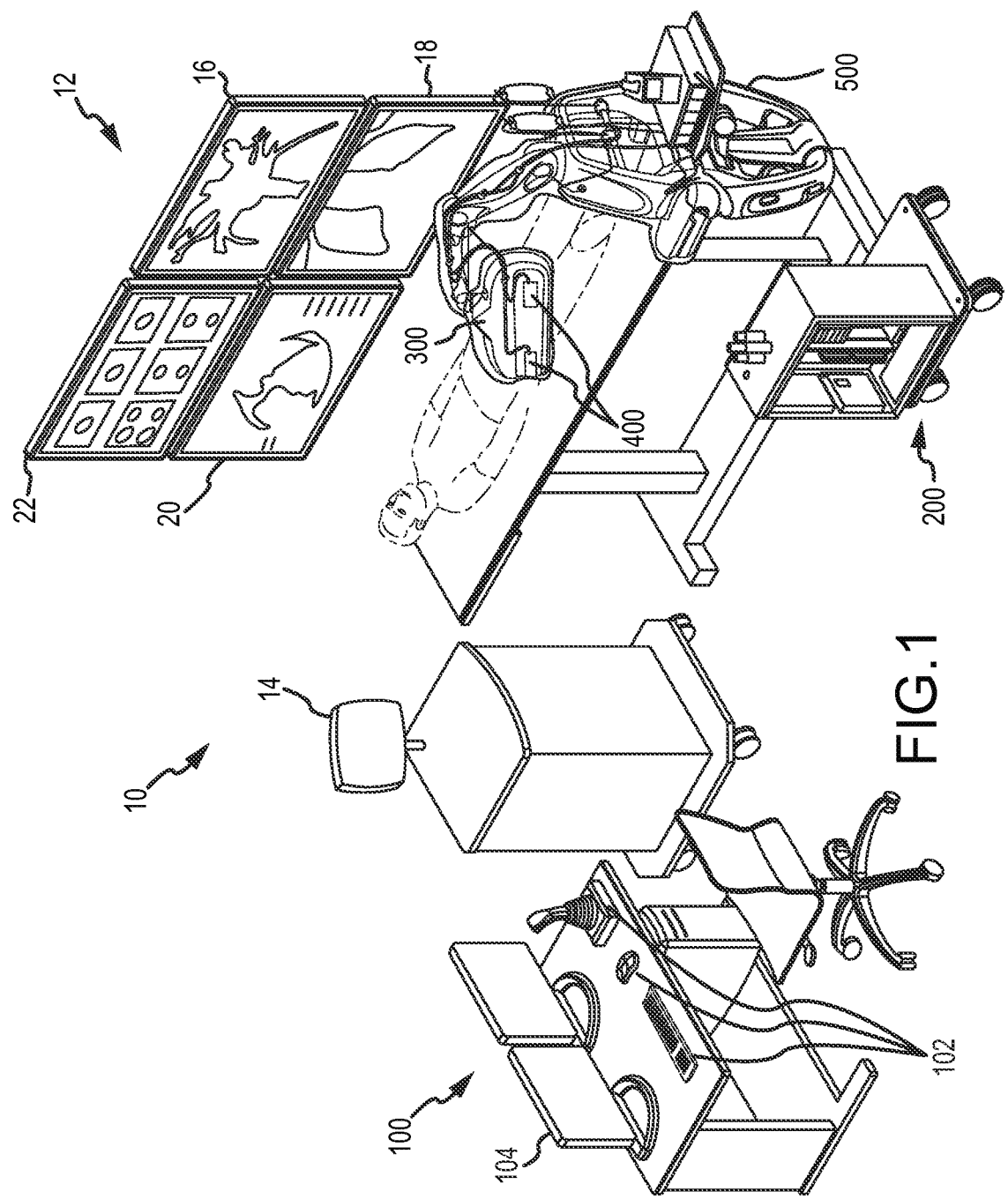
FIG. 1 is an isometric diagrammatic view of a robotic catheter system, illustrating an exemplary layout of various system components.

Now referring to the drawings wherein like reference numerals are used to identify identical components in the various views, FIG. 1 is a diagrammatic view of an exemplary RCGS 10.

Exemplary RCGS System Description.

RCGS 10 can be likened to power steering for a catheter system. The RCGS 10 can be used, for example, to manipulate the location and orientation of catheters and sheaths in a heart chamber or in another body cavity or lumen. The RCGS 10 thus provides the user with a similar type of control provided by a conventional manually-operated system, but allows for repeatable, precise, and dynamic movements. For example, a user such as an electrophysiologist can identify locations (potentially forming a path) on a rendered computer model of the cardiac anatomy. The system can be configured to relate those digitally selected points to positions within a patient's actual/physical anatomy, and can thereafter command and control the movement of the catheter to the defined positions. Once at the specified target position, either the user or the system can perform the desired diagnostic or therapeutic function. The RCGS 10 enables full robotic navigation/guidance and control.

As shown in FIG. 1, the RCGS 10 can generally include one or more monitors or displays 12, a visualization, mapping and navigation (including localization) system 14, a human input device and control system (referred to as "input control system") 100, an electronic control system 200, a manipulator assembly 300 for operating a device cartridge 400, and a manipulator support structure 500 for positioning the manipulator assembly 300 in proximity to a patient or a patient's bed.

Displays 12 are configured to visually present to a user information regarding patient anatomy, medical device location or the like, originating from a variety of different sources. Displays 12 can include (1) an ENSITE VELOCITY monitor 16 (coupled to system 14—described more fully below) for displaying cardiac chamber geometries or models, displaying activation timing and voltage data to identify arrhythmias, and for facilitating guidance of catheter movement; (2) a fluoroscopy monitor 18 for displaying a real-time x-ray image or for assisting a physician with catheter movement; (3) an intra-cardiac echo (ICE) display 20 to provide further imaging; and (4) an EP recording system display 22.

The system 14 is configured to provide many advanced features, such as visualization, mapping, navigation support and positioning (i.e., determine a position and orientation (P&O) of a sensor-equipped medical device, for example, a P&O of a distal tip portion of a catheter). Such functionality can be provided as part of a larger visualization, mapping and navigation system, for example, an ENSITE VELOCITY system running a version of ENSITE NAVX® software commercially available from St. Jude Medical, Inc., of St. Paul, Minn. and as also seen generally by reference to U.S. Pat. No. 7,263,397 entitled "METHOD AND APPARATUS FOR CATHETER NAVIGATION AND LOCATION AND MAPPING IN THE HEART" to Hauck et al., owned by the common assignee of the present disclosure, and hereby incorporated by reference in its entirety as though fully set forth herein. System 14 can comprise conventional apparatus known in the art, for example, the ENSITE VELOCITY system described above or other known technologies for locating/navigating a catheter in space (and for visualization), including, for example, the CARTO visualization and location system of Biosense Webster, Inc., the AURORA® system of Northern Digital Inc., a magnetic field based localization system such as the gMPS system based on technology from MediGuide Ltd. of Haifa, Israel and now owned by St.

Jude Medical, Inc. (e.g., as exemplified by U.S. Pat. Nos. 7,386,339, 7,197,354 and 6,233,476, all of which are hereby incorporated by reference in their entireties as though fully set forth herein) or a hybrid magnetic field-impedance based system, such as the system described in U.S. patent application Ser. No. 13/231,284, entitled "CATHETER NAVIGATION USING IMPEDANCE AND MAGNETIC FIELD MEASUREMENTS", or the CARTO 3 visualization and location system of Biosense Webster, Inc. Some of the localization, navigation and/or visualization systems can involve providing a sensor for producing signals indicative of catheter location and/or orientation information, and can include, for example, one or more electrodes in the case of an impedance-based localization system such as the ENSITE VELOCITY system running ENSITE NAVX® software, which electrodes can already exist in some instances, or alternatively, one or more coils (i.e., wire windings) configured to detect one or more characteristics of a low-strength magnetic field, for example, in the case of a magnetic-field based localization system such as the gMPS system using technology from MediGuide Ltd. described above.

The input control system 100 is configured to allow a user, such as an electrophysiologist, to interact with the RCGS 10, in order to control the movement and advancement/withdrawal of both a catheter and sheath (see, e.g., commonly assigned U.S. patent application Ser. No. 12/751,843 filed Mar. 31, 2010 entitled "ROBOTIC CATHETER SYSTEM" and PCT/US2009/038597 entitled "ROBOTIC CATHETER SYSTEM WITH DYNAMIC RESPONSE", published as WO 2009/120982; the disclosures of both applications being hereby incorporated by reference in their entireties as though fully set forth herein). Generally, several types of input devices and related controls can be employed, including, without limitation, instrumented traditional catheter handle controls, oversized catheter models, instrumented user-wearable gloves, touch screen display monitors, 2-D input devices, 3-D input devices, spatially detected styluses, and traditional joysticks. For a further description of exemplary input apparatus and related controls, see, for example, commonly assigned U.S. patent application Ser. No. 12/933,063 entitled "ROBOTIC CATHETER SYSTEM INPUT DEVICE" and U.S. patent application Ser. No. 12/347,442 entitled "MODEL CATHETER INPUT DEVICE", the entire disclosures of both applications being hereby incorporated by reference in their entireties as though fully set forth herein. The input devices can be configured to directly control the movement of the catheter and sheath, or can be configured, for example, to manipulate a target or cursor on an associated display.

In an embodiment, a touch screen display capable of receiving input from multiple users simultaneously (i.e., a multi-user touch screen display) is both the main component of the user input control system 100 and replaces one or more of the displays 12. In such an embodiment, other components of the user input control system 100 may also be used, such as a mouse, keyboard, and joystick. Multi-user touch-based control of the RCGS 10 is described in detail in conjunction with FIGS. 9-13.

The electronic control system 200 is configured to translate (i.e., interpret) inputs (e.g., motions) of the user at an input device or from another source into a resulting movement of the catheter and/or surrounding sheath. In this regard, the system 200 includes a programmed electronic control unit (ECU) in communication with a memory or other computer readable media (memory) suitable for information storage. The electronic control system 200 is configured, among other things, to issue commands (i.e., actuation control signals) to the manipulator assembly 300 (i.e., to the actuation units—electric motors) to move or bend the catheter and/or sheath to prescribed positions and/or in prescribed ways, all in accordance with the received user input and a predetermined operating strategy programmed into the system 200. In addition to the instant description, further details of a programmed electronic control system can be found in commonly assigned U.S. patent application Ser. No. 12/751,843 filed Mar. 31, 2010 entitled "ROBOTIC CATHETER SYSTEM", described above. It should be understood that although the exemplary ENSITE VELOCITY system 14 and the electronic control system 200 are shown separately, integration of one or more computing functions can result in a system including an ECU on which can be run both (i) various control and diagnostic logic pertaining to the RCGS 10 and (ii) the visualization, mapping and navigation functionality of system 14.

The manipulator assembly 300, in response to such commands, is configured to maneuver the medical device (e.g., translation movement, such as advancement and withdrawal of the catheter and/or sheath), as well as to effectuate distal end (tip) deflection and/or rotation or virtual rotation. In an embodiment, the manipulator assembly 300 can include actuation mechanisms/units (e.g., a plurality of electric motor and lead screw combinations, or other electric motor configurations, as detailed below) for linearly actuating one or more control members (e.g., steering wires) associated with the medical device for achieving the above-described translation, deflection and/or rotation (or virtual rotation). In addition to the description set forth herein, further details of a manipulator assembly can be found in commonly assigned U.S. patent application Ser. No. 12/347,826 titled "ROBOTIC CATHETER MANIPULATOR ASSEMBLY", the disclosure of which is hereby incorporated by reference in its entirety as though fully set forth herein.

A device cartridge 400 is provided for each medical device controlled by the RCGS 10. For this exemplary description of an RCGS, one cartridge is associated with a catheter and a second cartridge is associated with an outer sheath. The cartridge is then coupled, generally speaking, to the RCGS 10 for subsequent robotically-controlled movement. In addition to the description set forth herein, further details of a device cartridge can be found in commonly owned U.S. patent application Ser. No. 12/347,835 entitled "ROBOTIC CATHETER DEVICE CARTRIDGE" and U.S. patent application Ser. No. 12/347,842 entitled "ROBOTIC CATHETER ROTATABLE DEVICE CARTRIDGE", the disclosures of both applications being hereby incorporated by reference in their entireties as though fully set forth herein.

Figure 2:
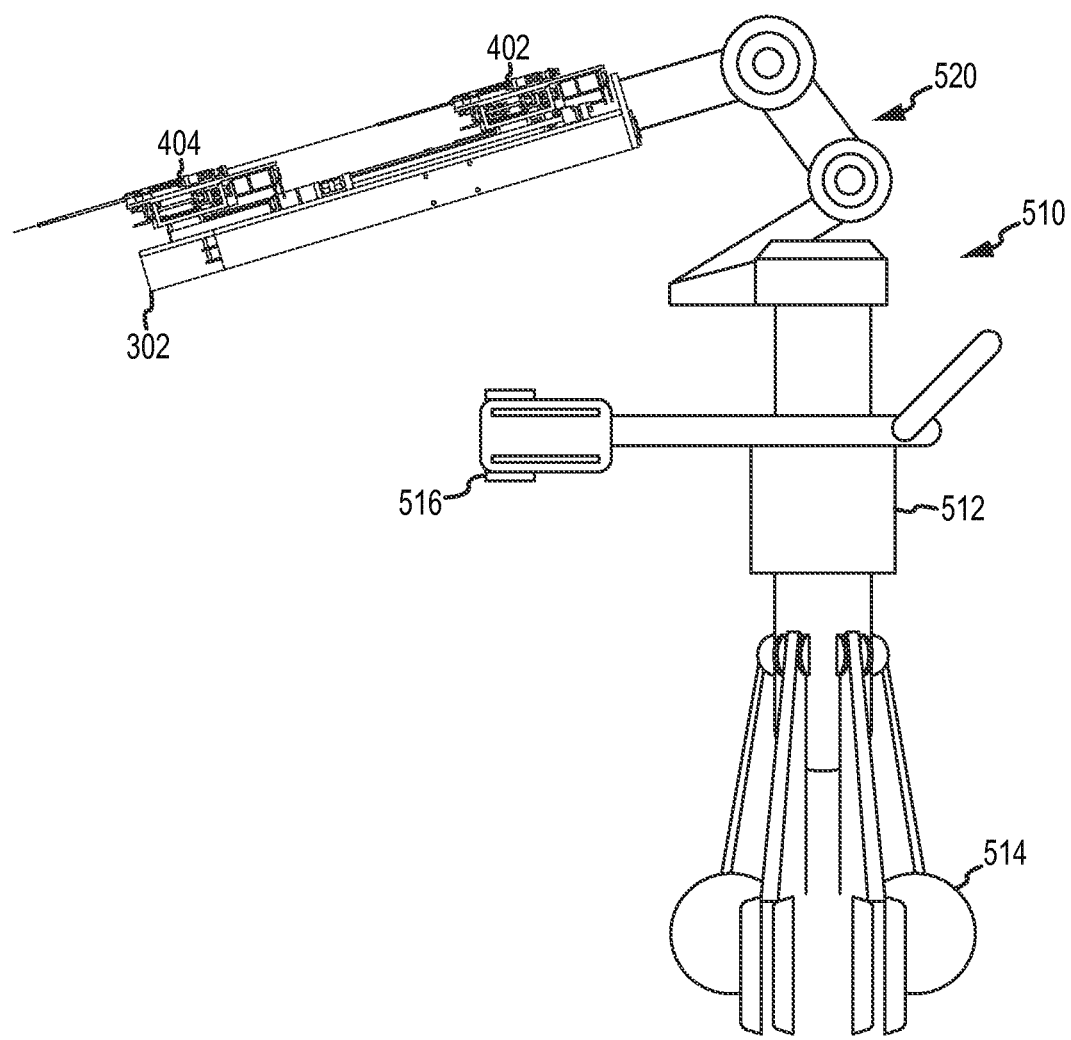
FIG. 2 is a side view of a manipulator assembly shown in FIG. 1, coupled to a robotic support structure, showing side views of catheter and sheath manipulation mechanisms.

FIG. 2 is a side view of an exemplary robotic catheter manipulator support structure, designated structure 510 (see commonly owned U.S. patent application Ser. No. 12/347,811 entitled "ROBOTIC CATHETER SYSTEM" described above). The structure 510 can generally include a support frame 512 including retractable wheels 514 and attachment assembly 516 for attachment to an operating bed (not shown). A plurality of support linkages 520 can be provided for accurately positioning one or more manipulator assemblies, such as manipulator assembly 302. The assembly 302 is configured to serve as the interface for the mechanical control of the movements or actions of one or more device cartridges, such as catheter and sheath cartridges 402, 404 described below. Each device cartridge is configured to receive and retain a respective proximal end of an associated medical device (e.g., catheter or sheath). The assembly 302 also includes a plurality of manipulation bases onto which the device cartridges are mounted. After mounting, the manipulator assembly 302, through the manipulation bases, is capable of manipulating the attached catheter and sheath.

Figure 3A:
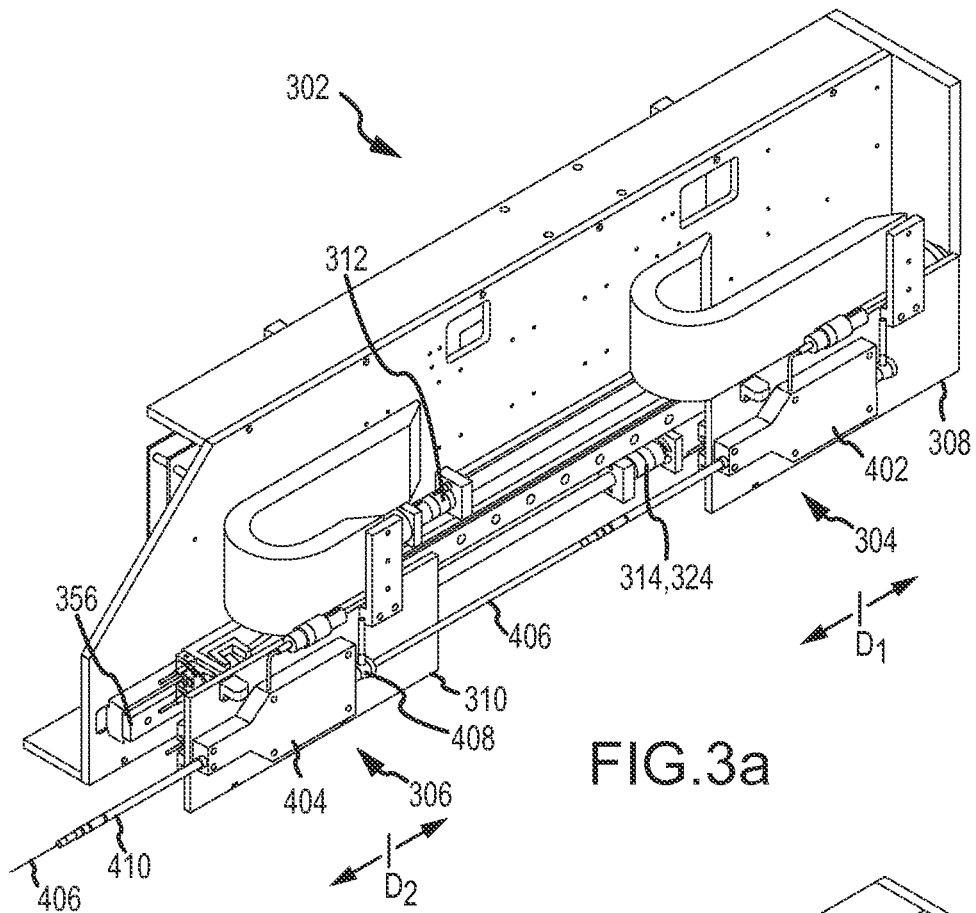
FIGS. 3a-3b are isometric views of a manipulator assembly shown in FIG. 2, showing the catheter and sheath manipulation mechanism in greater detail.
Figure 3B:
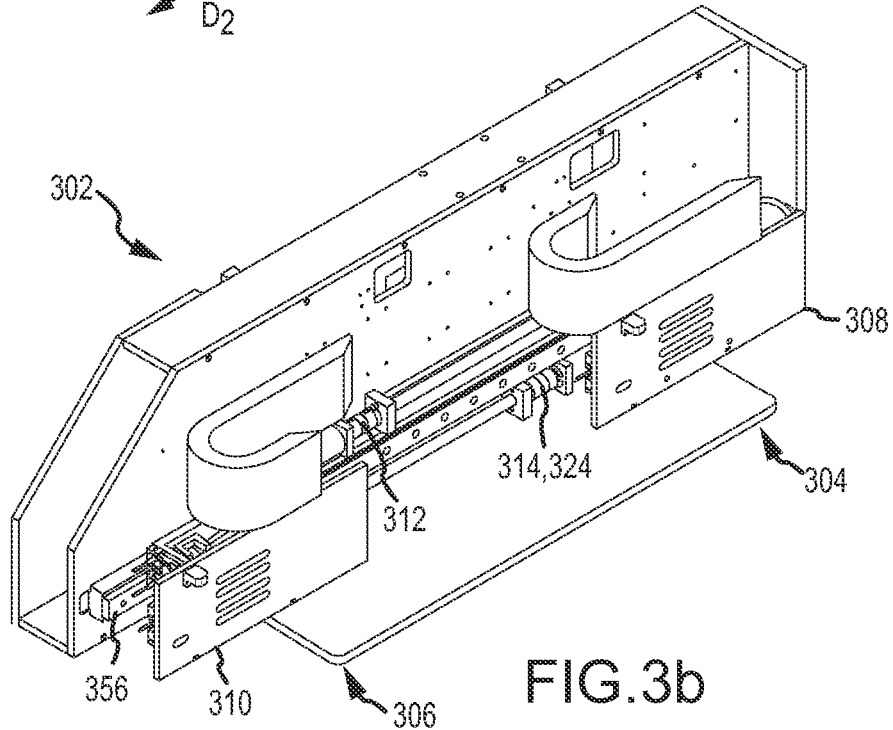
Figure 4A:
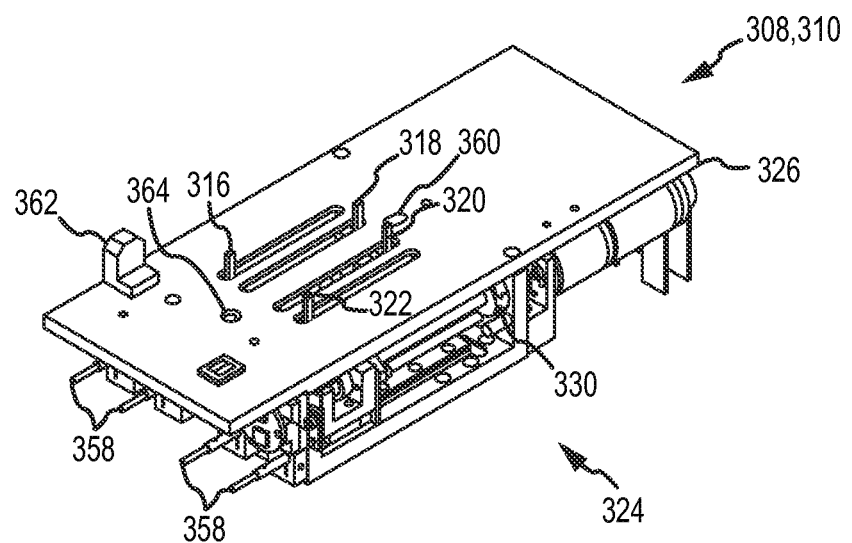
FIGS. 4a-4c are isometric views showing a sheath manipulation base of FIGS. 3a-3b in greater detail.
Figure 4B:
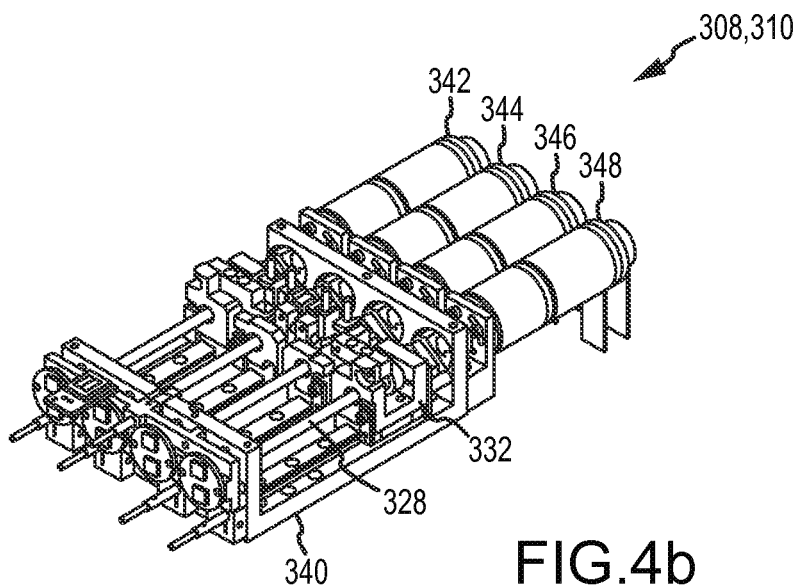
Figure 4C:
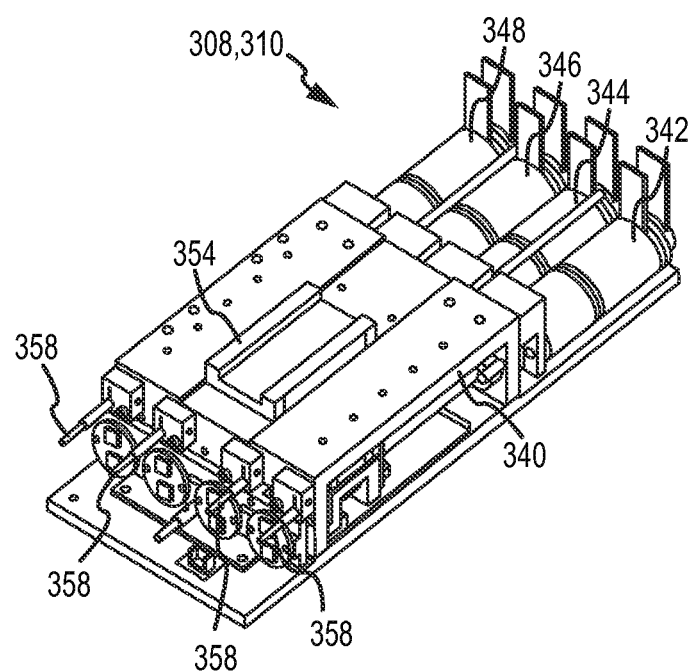
Figure 5A:
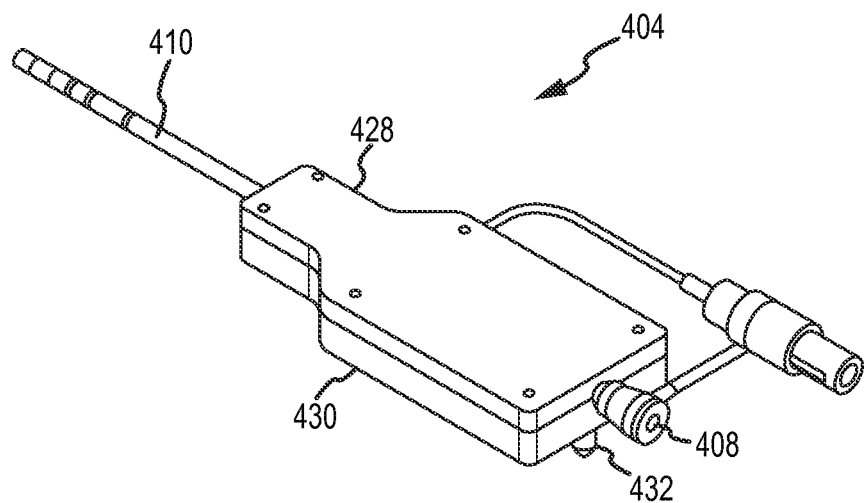
FIGS. 5a-5b are isometric views showing a sheath cartridge of FIGS. 3a-3b in greater detail.
Figure 5B:
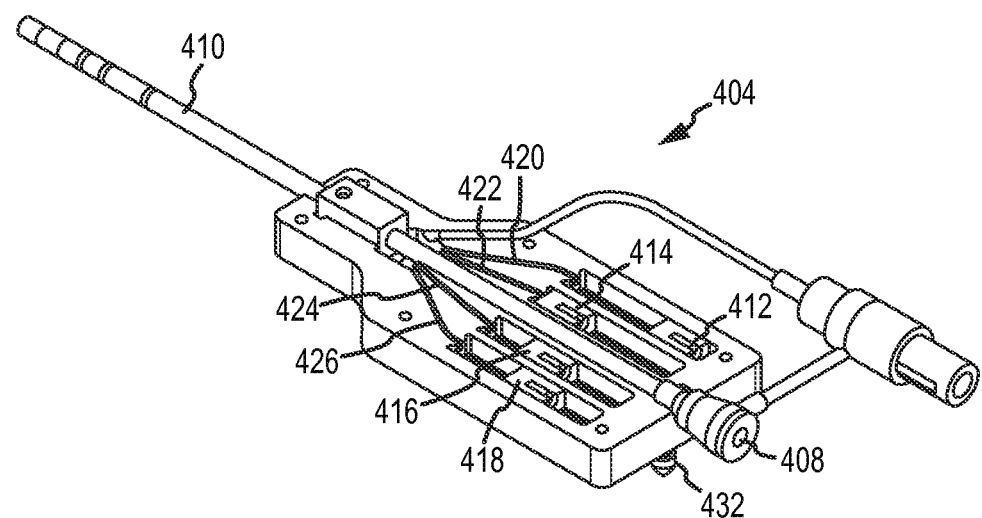

In the Figures to follow, FIGS. 3a-3b will show a manipulator assembly, FIGS. 4a-4c will show a manipulation base, and FIGS. 5a-5b will show a device cartridge.

FIG. 3a is an isometric view, with portions omitted for clarity, of manipulator assembly 302. Assembly 302 includes a catheter manipulator mechanism 304, a sheath manipulator mechanism 306, a catheter manipulation base 308, a sheath manipulation base 310, a first (catheter) drive mechanism 312, a second (sheath) drive mechanism 314, and a track 356. As further shown, assembly 302 further includes a catheter cartridge 402 and a sheath cartridge 404, with a catheter 406 having a proximal end opening 408 coupled to the catheter cartridge 402 and a sheath 410 coupled to the sheath cartridge 404.

Catheter and sheath manipulator mechanisms 304, 306 are configured to manipulate the several different movements of the catheter 406 and the sheath 410. First, each mechanism 304, 306 is configured to impart translation movement to the catheter 406 and the sheath 410. Translation movement here refers to the independent advancement and retraction (withdrawal) as shown generally in the directions designated D1 and D2 in FIG. 3a. Second, each mechanism 304, 306 is also configured to effect deflection of the distal end of either or both of the catheter and sheath 406, 410. Third, each mechanism 304, 306 can be operative to effect a so-called virtual (omni-directional) rotation of the distal end portion of the catheter 406 and the sheath 410. Virtual rotation, for example, can be made through the use of independent four-wire steering control for each device (e.g., eight total steering wires, comprising four sheath control wires and four catheter control wires). The distal end movement is referred to as "virtual" rotation because the outer surface of the sheath (or catheter) does not in fact rotate in the conventional sense (i.e., about a longitudinal axis) but rather achieves the same movements as conventional uni-planar deflection coupled with axial rotation. In addition to the present description of virtual rotation, further details can be found in PCT/US2009/038597 entitled "ROBOTIC CATHETER SYSTEM WITH DYNAMIC RESPONSE", published as WO 2009/120982.

Each manipulator mechanism 304, 306 further includes a respective manipulation base 308, 310 onto which are received catheter and sheath cartridges 402, 404. Each interlocking base 308, 310 can be capable of travel in the longitudinal direction of the catheter/sheath (i.e., D1, D2 respectively) along a track 356. In an embodiment, D1 and D2 can each represent a translation of approximately 8 linear inches. Each interlocking base 308, 310 can be translated by a respective high precision drive mechanism 312, 314. Such drive mechanisms can include, for example and without limitation, an electric motor driven lead screw or ball screw.

The manipulator mechanisms 304, 306 are aligned with each other such that the catheter 406 can pass through the sheath 410 in a coaxial arrangement. Thus, the sheath 410 can include a water-tight proximal sheath opening 408. Overall, the manipulator mechanisms 304, 306 are configured to allow not only coordinated movement but also relative movement between catheter and sheath cartridges 402, 404 (and thus relative movement between catheter and sheath).

FIG. 3b is an isometric view of manipulator assembly 302, substantially the same as FIG. 3a except that catheter and sheath cartridges 402, 404 are omitted (as well as catheter and sheath 406, 410) so as to reveal an exposed face of the manipulation bases 308, 310.

FIG. 4a is an isometric, enlarged view showing manipulation base 308 (and base 310) in greater detail. Each cartridge 402, 404 has an associated manipulation base 308, 310. Each base 308, 310 can include a plurality of fingers 316, 318, 320 and 322 (e.g., one per steering wire) that extend or protrude upwardly to contact and interact with steering wire slider blocks (i.e., such as slider blocks 412, 414, 416, 418, best shown in FIG. 5b) to independently tension select steering wires 420, 422, 424, 426 (also best shown in FIG. 5b). Each finger can be configured to be independently actuated (i.e., moved back and forth within the oval slots depicted in FIG. 4a) by a respective precision drive mechanism, such as a motor driven ball screw 324. A plate 326 provides a surface onto which one of the cartridges 402, 404 are seated.

FIG. 4b is an isometric, enlarged view of base 308 (and base 310), substantially the same as FIG. 4a except with plate 326 omitted. Each motor-driven ball screw 324 (i.e., for both finger control and for cartridge translation control) can further include encoders to measure a relative and/or an absolute position of each element of the system. Moreover, each motor-driven ball screw 324 (i.e., for both finger control and cartridge translation control) can be outfitted with steering wire force sensors to measure a corresponding steering wire tension. For example, a corresponding finger 316, 318, 320 or 322 can be mounted adjacent to a strain gauge for measuring the corresponding steering wire tension. Each motor-driven ball screw 324 can include a number of components, for example only, a rotary electric motor (e.g., motors 342, 344, 346 and 348), a lead screw 328, a bearing 330 and a coupler 332 mounted relative to and engaging a frame 340. In the depicted embodiments linear actuation is primarily, if not exclusively, employed. However, some known examples of systems with rotary-based device drivers include United States Patent Publication No. 2009/0012533 entitled "Robotic Instrument Control System" and United States Patent Publication No. 2008/0249536 entitled "INTERFACE ASSEMBLY FOR CONTROLLING ORIENTATION OF ROBOTICALLY CONTROLLED MEDICAL INSTRUMENT", the disclosures of which are hereby incorporated by reference in their entireties as though fully set forth herein.

FIG. 4c is an isometric, enlarged view of base 308 (and base 310) that is taken from an opposite side as compared to FIGS. 4a-4b. Bases 308, 310 can include components such as a plurality of electrically-operated motors 342, 344, 346 and 348, respectively coupled to fingers 316, 318, 320 and 322. A bearing 354 can be provided to facilitate the sliding of bases 308, 310 on and along track 356. A plurality of inductive sensors (e.g. home sensors) 358 can also be provided for guiding each manipulation base to a home position.

FIG. 5a is an isometric, enlarged view showing, in greater detail, sheath cartridge 404. It should be understood that the description of sheath cartridge 404, except as otherwise stated, applies equally to catheter cartridge 402. Catheter 406 and sheath 410 can be substantially connected or affixed to respective cartridges 402, 404 (e.g., in the neck portion). Thus, advancement of cartridge 404 correspondingly advances the sheath 410 and retraction of cartridge 404 retracts the sheath 410. Likewise, although not shown, advancement of cartridge 402 correspondingly advances catheter 406 while a retraction of cartridge 402 retracts catheter 406. As shown, sheath cartridge 404 includes upper and lower cartridge sections 428, 430.

FIG. 5b is an isometric, enlarged view showing, in greater detail, sheath cartridge 404, with upper section 428 omitted to reveal interior components. Cartridge 404 can include slider blocks (e.g., as shown for cartridge 404, slider blocks 412, 414, 416, 418), each rigidly and independently coupled to a respective one of a plurality of steering wires (e.g., sheath steering wires 420, 422, 424, 426) in a manner that permits independent tensioning of each steering wire. Likewise, cartridge 402 for catheter 406 also includes slider blocks for coupling to a plurality (i.e., four) steering wires. Device cartridges 402, 404 can be provided as a disposable item that is capable of being easily positioned (e.g., snapped) into place (i.e., onto a respective base 408, 410). Sheath cartridge 404 can be designed in a similar manner as the catheter cartridge 402, but will typically be configured to provide for the passage of catheter 406.

Referring to FIGS. 4a and 5a, catheter and sheath cartridges 402, 404 are configured to be secured or locked down onto respective manipulation bases 308, 310. To couple cartridge 402 (and 404) with base 308 (and 310), one or more locking pins (e.g., 432 in FIG. 5a) on the cartridge can engage one or more mating recesses 360 in the base (see FIG. 4a). In an embodiment, such recesses 360 can include an interference lock such as a spring detent or other locking means. In an embodiment, such other locking means can include a physical interference that can require affirmative/positive action by the user to release the cartridge. Such action can include or require actuation of a release lever 362. Additionally, the cartridge can include one or more locator pins (not shown) configured to passively fit into mating holes on the base (e.g., 364 in FIG. 4a).

In operation, a user first manually positions catheter 406 and sheath 410 (with catheter 406 inserted in sheath 410) within the vasculature of a patient. Once the medical devices are roughly positioned in relation to the heart or other anatomical site of interest, the user can then engage or connect (e.g., "snap-in") the catheter and sheath cartridges into place on respective bases 308, 310. When a cartridge is interconnected with a base, the fingers fit into the recesses formed in the slider blocks. For example, with respect to the sheath cartridge 404 and sheath base 310, each of the plurality of fingers 316, 318, 320 or 322 fit into corresponding recesses formed between the distal edge of slider blocks 412, 414, 416, 418 and a lower portion of the cartridge housing (best shown in FIG. 5b). Each finger can be designed to be actuated in a proximal direction to respectively move each slider block, thereby placing the respective steering wire in tension (i.e., a "pull" wire). Translation, distal end bending, and virtual rotation can be accomplished through the use of the RCGS 10.

Figure 6:
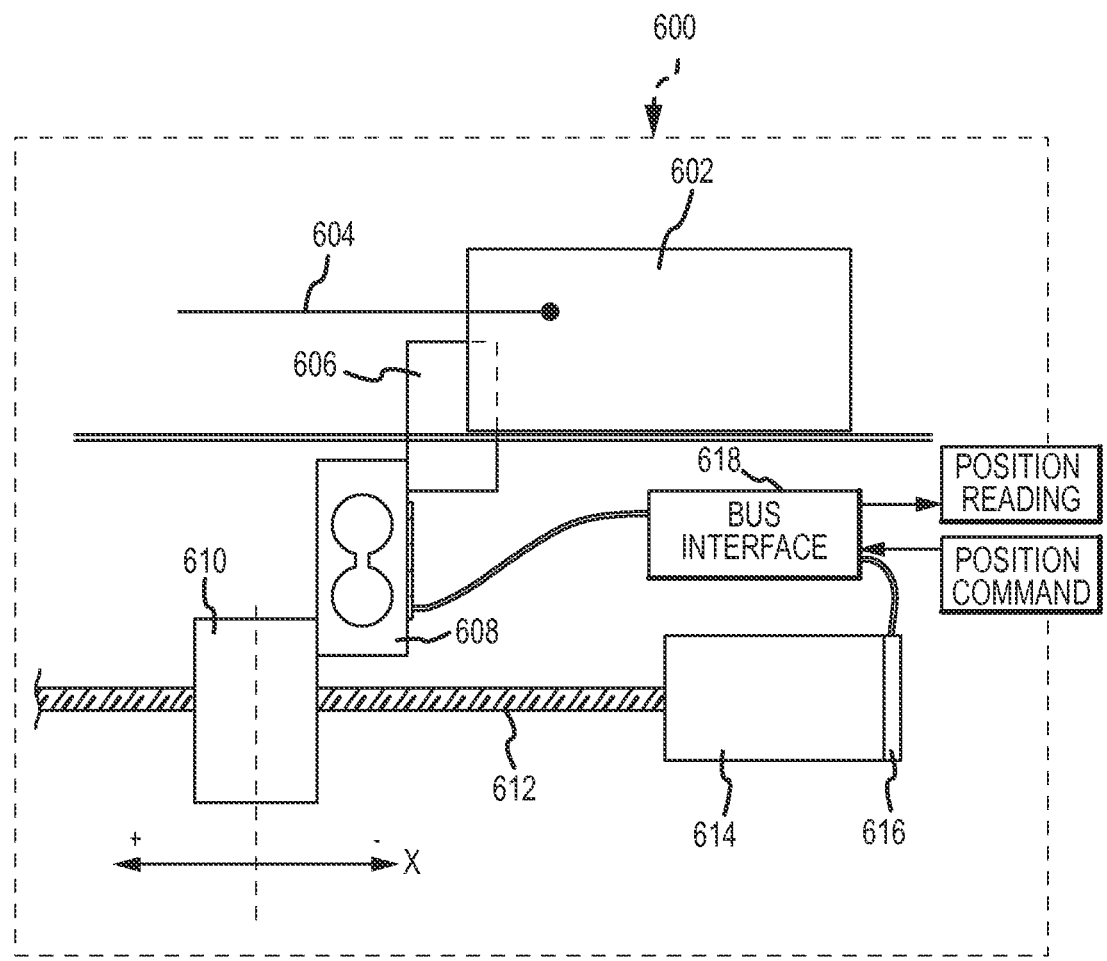
FIG. 6 is a diagrammatic view of the sheath manipulation mechanism of FIG. 2.

FIG. 6 is a diagrammatic view of a node suitable for connection to a communications bus (not shown) in RCGS 10. The node includes an actuation unit 600, similar to the actuation mechanisms described above (e.g., catheter actuation mechanism 304). The RCGS 10 can have at least ten such actuation units (i.e., one for each of the four catheter steering wires, four sheath steering wires, one catheter manipulation base and one sheath manipulation base), which, as described, include electric motors.

FIG. 6 shows in diagrammatic or block form many of the components described above—where appropriate, references to the earlier describe components will be made. Actuation unit 600 includes a first, slidable control member 602 (i.e., slider as described above) that is connected to or coupled with a second, tensile control member 604 (i.e., steering wire as described above). The slider 602 can be configured to interface with a third, movable control member 606 (i.e., finger as described above). The finger 606 can further be operatively coupled with a portion of a sensor 608 (e.g., a force sensor), which, in turn, can be coupled with a translatable drive element 610 that can be mechanically moved. For example, without limitation, translatable drive element 610 can ride on or can otherwise be mechanically moved by a mechanical movement device 612 that, in turn, can be coupled with an electric motor 614. The mechanical movement device 612 can comprise a lead screw while the translatable drive element 610 can comprise a threaded nut, which can be controllably translated by screw 612 in the X+ or X− directions. In another embodiment, mechanical movement device 612 can include a ball screw, while translatable drive element 610 can include a ball assembly. Many variations are possible, as will be appreciated by one of ordinary skill in the art.

The actuation unit 600 also includes a rotary motor position encoder 616 that is coupled to the motor 614 and is configured to output a signal indicative of the position of the motor 614. The encoder 616 can comprise an internal, optical encoder assembly, integral with motor 614, configured to produce a relatively high accuracy output. The motor position sensor can operate in either absolute or relative coordinates. In an embodiment, a second motor position sensor (not shown) can also be provided, such as a potentiometer (or impedance-based), configured to provide a varying voltage output proportional to the motor's rotary position. The output of the secondary position sensor can be used as an integrity check of the operating performance of the primary position sensor (encoder) during start-up or initialization of the actuation unit.

Actuation unit 600 also includes one or more local controllers including a bus interface 618 to facilitate exchange of information between actuation unit 600 and electronic control system 200 (via the bus). The controller communicates with the main electronic control system 200 via the bus interface and is configured, among other things, to (1) receive and execute motor actuation commands issued by the electronic control system 200 for controlling the movements of motor 614; and (2) receive and execute a command (issued by the electronic control system 200) to take a motor position sensor reading, for example, from encoder 616 and subsequently report the reading to system 200.

Figure 7:
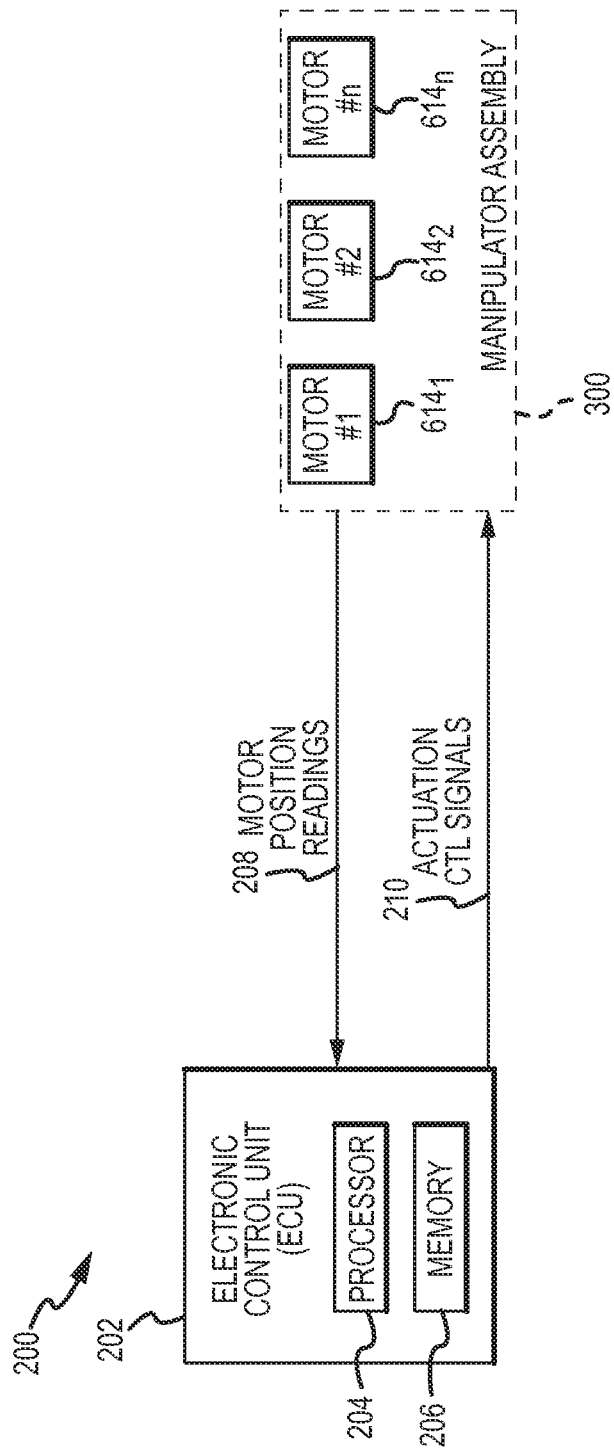
FIG. 7 is a block diagram of the electrical control system of FIG. 1.

FIG. 7 is a block diagram showing the electronic control system 200 of FIG. 1 in greater detail. The system 200 includes an ECU 202 having a processor 204 and an associated memory 206. The system 200 further includes logic, which in an embodiment can take the form of software stored in memory 206 and configured for execution by the processor 204, for performing at least the functionality described herein. The ECU 202 can comprise conventional apparatus known in the art. Generally, the ECU 202 is configured to perform core operating functions of the RCGS 10. Among other things, the ECU 202 is configured to generate graphical user interfaces, to interpret user inputs, device location data, motor position readings 208 and other inputs, and to generate a plurality of actuation control signals 210, which are provided to the manipulator assembly 300. The actuation control signals 210 in turn are configured to control the plurality of actuation units 600, and therefore, the plurality of electric motors $614_1, 614_2, \ldots, 614_n$, so as to actuate a plurality of control members of the medical device (e.g., pull wires for deflection movement, manipulation bases for translation movement).

Multi-User Touch-Based RCGS Control.

Figure 8:
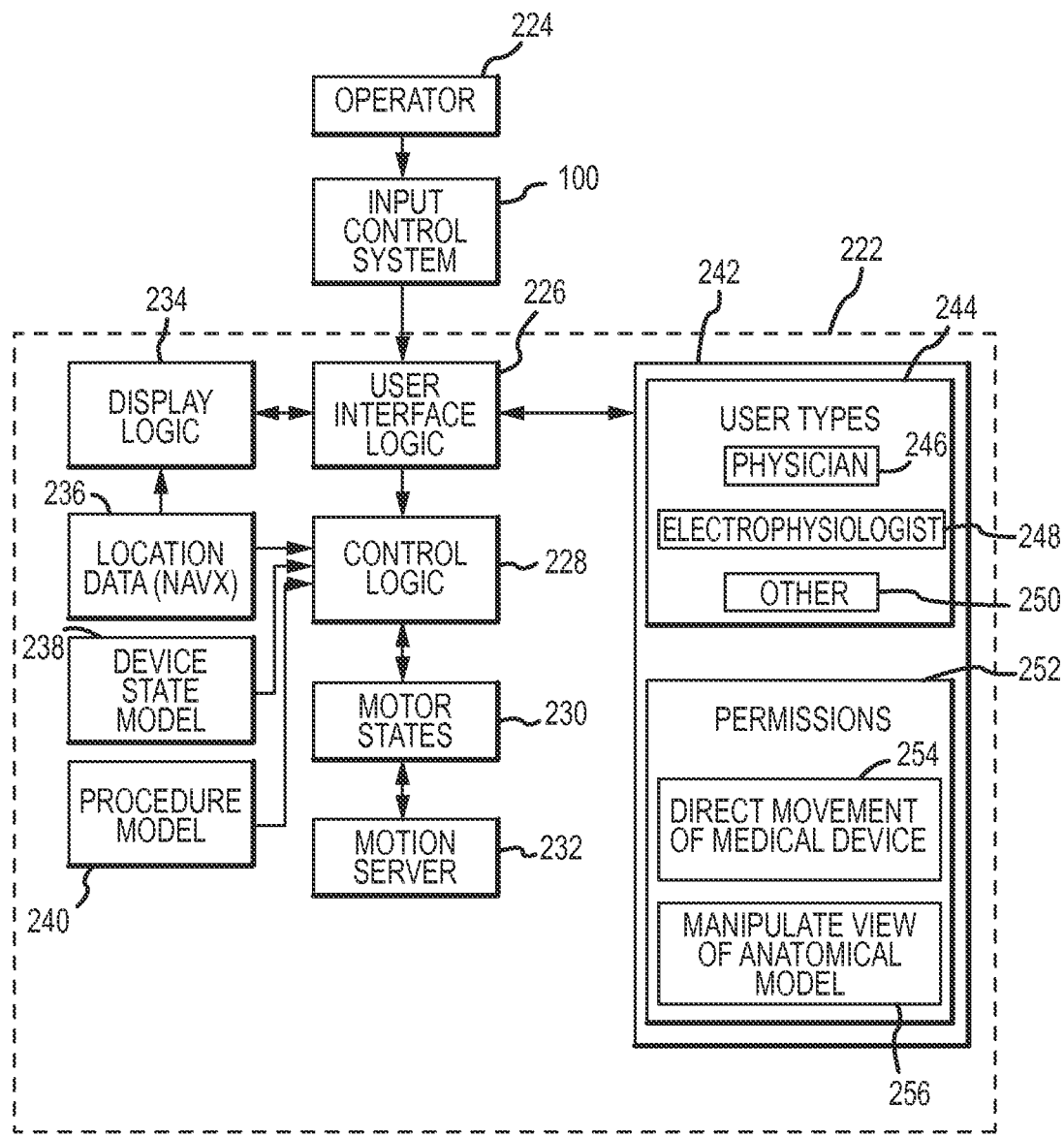
FIG. 8 is a block diagram of an exemplary embodiment of the electrical control system of FIG. 7.

FIG. 8 is block diagram of an embodiment 222 of the electronic control system 200. The control system 222 is configured for interaction with and by an operator/user 224. In many instances, the user 224 can refer, for example, to an electrophysiologist or physician that is manipulating the catheter via the RCGS 10. The system 222 includes user interface logic 226, control logic 228, a motor state model 230, a motion server 232, display logic 234, a source of location data 236, a device state model 238, a procedure model 240, and a memory portion 242 containing a set of user types 244 and a set of permissions 252.

The control system 222 receives inputs from the user 224 via user interface logic 226, which receives user input through the input control system 100. The operator 224 can use one or more of the user input devices 102 of the input control system 100 to perform such tasks as, for example and without limitation, inputting desired catheter motions, rotating an anatomical model on a workstation display, and the like. The user input devices 102 can be further configured to allow the user 224 to provide inputs with respect to the anatomical model of a body portion of the patient (e.g., for setting up a pre-planned path for the catheter, for initiating and conducting diagnostic and therapeutic procedures, etc.).

The display logic 234 provides views of anatomical models and rendered representations of medical devices. The display logic 234 may provide anatomical model views based on models stored in memory or based on real-time data and images. Stored models and real-time data may both be based on computed tomography (CT), magnetic resonance imaging (MRI), ultrasound, fluoroscopy, or other imaging modalities known in the art. Models may also include electrophysiological maps and other data associated with the subject of the model (e.g., the heart). Representations of medical devices (e.g., catheter 406 and sheath 410) may be rendered by the display logic 234 based on data about the current position, orientation, and/or shape of the device received from location data source 236.

The control logic 228 is configured to process incoming data from a plurality of sources, including the user interface logic 226, the location data source 236 (i.e., the visualization, navigation, and mapping system 14, for example), the motor state model 230 (e.g., to obtain the current motor states), and the device state model 238 and generate instructions for the RCGS 10 to effect movement of one or more medical devices. The control logic 228 can further be configured to generate a procedure model 240 containing a record of the data processed by the control logic 228 during a procedure or maintenance session.

The information from location data source 236 can comprise position and orientation information associated with the manipulated catheter and/or sheath, or a portion thereof such as the tip of the device. In an embodiment where an impedance-based visualization, navigation, and mapping system 14 (e.g., ENSITE VELOCITY) is used as the source 236, the location data can comprise at least electrode coordinates (x,y, z) for specified electrodes on the catheter 406 or sheath 410. This data can be used, for example, to generate models and maps of anatomical structures as well as to display the location and orientation of the electrodes and/or the tip of the catheter 406 relative to an anatomical structure of interest.

The motor state model 230 contains information about the current states for each of the motors in the RCGS 10 (i.e., reflects the current physical states of the physical motors). States can include motor position, motor speed, tension (i.e., pull wire tension), and motor temperature. The motion server 232 is configured to interpret movement commands in a way so as to achieve the motor states specified in the motor state model 230. The motor server 232 also communicates information to the motor state model 230 that describes the current physical states of the motors in the RCGS 10.

The device state model 238 contains information regarding the catheter 406 and/or sheath 410, including data from any diagnostic or therapeutic sensor present on the distal end of the catheter 406. The information included within the device state model 238 can include, for example, the make, model and physical dimensions of the catheter 406 and sheath 410 as well as data specific to different sensors attached to the catheter 406, that can include, for example, ablation tip temperature, ablation energy output, and catheter irrigation flow rate.

The procedure model 240 contains the information received and processed during operation of the RCGS 10, including received location data 238, data from motor state model 230, data from device state model 234, and user input received from the user interface logic 226, which allows a user 224 to later review and analyze a procedure. The control logic 228 can be configured to generate a procedure model 236 in the memory 206 of the ECU 202, or in another embodiment, be configured to record a procedure model 236 on an external storage device (e.g., CD, DVD, USB mass storage device, external hard disk drive) using a wired or wireless data network. Further, the control logic 228 can be configured to receive user input directing transmission of a procedure model 240 to a specified or preconfigured location or group using a wired or wireless data network. The control logic 228 can also be configured to retrieve a procedure model 240 from the memory 206 or an external storage device for analysis and display it in a graphical user interface generated by the ECU 202.

The user interface logic 226 is configured to generate a user interface that can be used to operate, control, and/or configure the RCGS 10. In an embodiment, the user interface logic 226 is configured to generate the user interface for display on a multi-user touch screen display. The interface provided can include anatomical model views, representations of robotically-controlled medical devices, other images such as fluoroscopic or ICE images, patient information such as ECG signals or data, and other information relevant to the procedure. The various elements provided in the interface can comprise a single video stream arranged by the user interface logic 226, or a number of video streams that are further arranged by the display. In a single-stream embodiment, the user interface logic 226 may be configured to arrange the graphical interface specifically so that it is appropriate for multi-user interaction (such as the interface shown in FIGS. 10a and 10b).

The user-interface logic 226 is configured to receive input from a variety of input devices and mechanisms, such as a touch screen display, mouse, keyboard, joystick, etc. The user interface logic 226 may also be configured to receive input in the form of verbal commands by a user through a microphone. Verbal commands may replace or be in addition to other input mechanisms, such as menu buttons. Verbal commands may be received by the user interface logic 226 to direct movement of a medical device, manipulate a graphical interface, or to perform other system functions such as connecting or disconnecting the ECU 202 to the rest of the robotic system, registering a medical device or other object with the robotic system, detaching a medical device from the robotic system, and recalibrating the effect of particular inputs.

The user interface logic 226 may be configured to receive touch-based input from a touch screen display in a variety of forms. For example, the UI logic 226 may receive input in the form of "gestures" from the touch screen display. Touch-based "gestures" can include, for example, swipe, tap, pinch, and many other known touch-based input motions. Each gesture may include, for example, a gesture type, a location, and for some gestures, a direction (e.g., for a swipe gesture). The UI logic 226 may also receive raw input data, where some gestures comprise multiple raw input data points (i.e., a swipe gesture may be a roughly linear series of individual raw input data points) each of which points can include a location, input pressure, and other data.

Each of the gestures noted above may be associated with respective input actions. For example, a swipe gesture may be used to move a medical device or to rotate a displayed anatomical model. A tap gesture may be used to select waypoints, to select a medical device on the screen for further input, or to prompt the display of data related to a device such as, for example, EP data from an electrode on the selected device displayed on a portion of the screen. A pinch gesture may be used to change the size of a displayed model (i.e., zoom out), or to change the size of a window (i.e., an interface portion in a multi-window display interface on the touch screen display, as described below in conjunction with FIGS. 10a-10b), or to entirely remove a window (i.e., interface portion) a portion thereof (i.e., a model or interface button displayed in the interface portion) from the display. Any gesture, including, but not limited to, those gestures mentioned above, may also prompt a popup button or query (provided, for example, by the UI logic 226) to approve the intended input before any action is taken to move a medical device or alter the displayed interface. In an embodiment, the user interface logic 226 may create and/or access a custom gesture set to associate particular gestures with particular input actions—i.e., the effect of particular gestures or particular raw input data (i.e., the effect of that input) may be customized for a particular system, user, or procedure.

In addition to providing the graphical user interface and receiving input through that interface and otherwise, the user interface logic 226 may be configured to interpret the received input (i.e., determine whether an input should result in medical device movement, model or other interface manipulation, or some other action). The UI data may be configured to interpret input based on either gesture data or raw input data. In an embodiment, the user interface logic may be configured to interpret simultaneous touch-based inputs from multiple users. After interpreting an input, the UI logic may, e.g., pass on the input to control logic 228 to effect robotic-controlled motion of a medical device or query an updated view of an anatomical model from display logic 234.

The user interface logic 226 may provide an interface that allows a user to perform system configuration functions. For example, the interface may include a mechanism used to register a medical device with the RCGS 10 or to allow the user to calibrate the relationship between a particular input and the resulting system action. The user interface provided by the user interface logic 226 may also include haptic feedback, for example, to inform a user when a controlled medical device is approaching or in contact with tissue or a target location. The provided haptic feedback may be through the entire touch screen display, or may be local to a particular location on the touch screen display. Haptic feedback may be based on the location, shape, and orientation of a medical device determined according to location data from source 236.

One potential issue inherent in using a multi-user touch screen display as an input device is the possibility that multiple users could direct the same robotically-controlled medical device at the same time. Without appropriate safeguards, such simultaneous control could lead to contradictory or redundant input by the multiple users that could result in unintended movement of the medical device. Accordingly, in an embodiment, the user interface logic 226 is configured to restrict guidance of each robotically-controlled medical device to a single user at a time. To achieve this restriction, the user interface logic 226 may be configured to associate each received touch-based input with a particular user or user type from the set of user types 244 and to only allow a single user or user type at a time to direct the movement of a particular medical device. Alternatively, simultaneous control can be prevented with a hierarchy of users such that the input of a higher-priority user is not overridden by the input of a lower-priority user. For example, if a physician or electrophysiologist is moving or has instructed the movement of a medical device, other users cannot override that movement. This restriction may be designed to prevent any secondary user overriding the input of a physician or electrophysiologist (whether intentionally or inadvertently) by, e.g., providing a popup confirmation window warning of the attempted override and asking for assent to the override.

Each user or user type may be associated with one or more permissions selected from the stored permissions set 252. Permissions can include, for example, permission to direct the movement of a medical device (shown as permission 254) and permission to manipulate a view of an anatomical model (shown as permission 256). Additional or alternate permissions may be stored and associated with users as well. In an embodiment, a physician user type 246 may be associated with both permissions 254, 256—i.e., the physician may manipulate an anatomical model view as well as direct the movement of a medical device. An electrophysiologist user type 248 may have similar permissions. In contrast, another user type 250 (i.e., a user other than a physician or an electrophysiologist) may only have permission to manipulate an anatomical model view 256. Likewise, a user may only be able to manipulate a view on a particular window or interface portion such that similar views on different windows or interface portions are sized or rotated separately.

To determine the proper interpretation of an input after associating it with a user or user type, the user interface logic 226 may consult the permissions associated with the user or user type. Based on the user or user type associated with an input and the permissions associated with the user or user type, the user interface logic 226 can determine whether an input should result in a medical device movement or some other action. For example, if a swipe motion is made on an anatomical model, the swipe could indicate either a command to manipulate the model itself (e.g., rotate, pan) or a command to direct a medical device to traverse the path indicated by the swipe. If the user interface logic 226 associates the input with a user type having permission to direct a medical device 254, the user interface logic 226 may then interpret the input as a medical device movement command and pass on the input to the control logic 228. If, on the other hand, the user interface logic 226 associates the input with a user type having permission to manipulate the model view 256, but without permission to direct medical device movement 254, the user interface logic may interpret the input as a model view manipulation command and forward the command to the display logic 234. Likewise, a particular motion may have different results based on the origin and termination points of the motion. For example, a swipe that starts on an image or representation of an ablation electrode may be used to drag an ablation catheter along a line to ablate a linear lesion, whereas a swipe starting on an image or representation of a diagnostic catheter or a secondary diagnostic electrode of an ablation catheter may indicate a simple movement of the catheter from one physical location to another. Likewise, the speed of the swipe may indicate the speed that the catheter is to be moved, as may the pressure used for the touch-based input. Furthermore, the system (e.g., via UI logic 226 or display logic 234) may highlight the medical device to be moved to give a user visual confirmation of the action. The highlighting may include selecting a highlight color that corresponds to the motion.

The user interface logic 226 may associate an input with a user or user type in a variety of ways. First, the user interface logic 226 may associate a discrete portion of the graphical interface, or particular inputs, with a particular user or users. For example, a portion of the graphical interface containing a representation of a medical device may be associated with a physician or electrophysiologist user type, and another portion of the same interface containing a view of an anatomical model may be associated with all user types. Second, biometric data may accompany the input, such as fingerprint data for a touch-based input or voice data for a verbal command. The user interface logic 226 may compare the biometric data to stored biometric data to confirm user identity, then determine the user type and associated permissions of that user to interpret the input, as described above.

In sum, the control system 222 implements a predetermined operating control strategy (i.e., higher level control algorithms) for the RCGS 10, as described in greater detail in U.S. Patent Publication No. 2010/0256558 entitled "ROBOTIC CATHETER SYSTEM", referenced above. Based on user inputs, as well as other inputs as described herein, the control system 222 outputs actuation control signals destined for the plurality of motors to achieve the desired catheter or sheath movements (i.e., translation, deflection or virtual rotation).

Figure 9A:
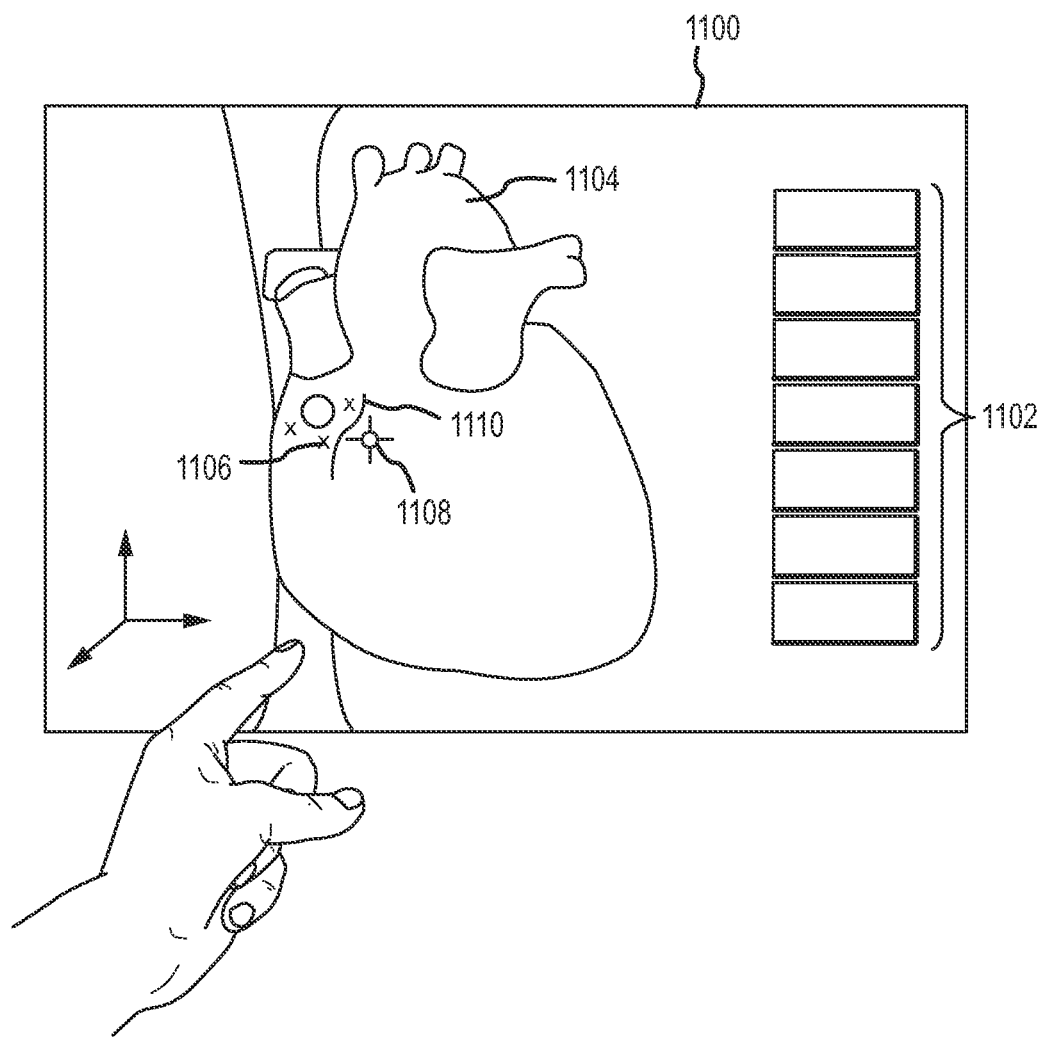
FIGS. 9a-9b are exemplary user interface portions for use with a touch-sensitive input device in a robotic catheter system.
Figure 9B:
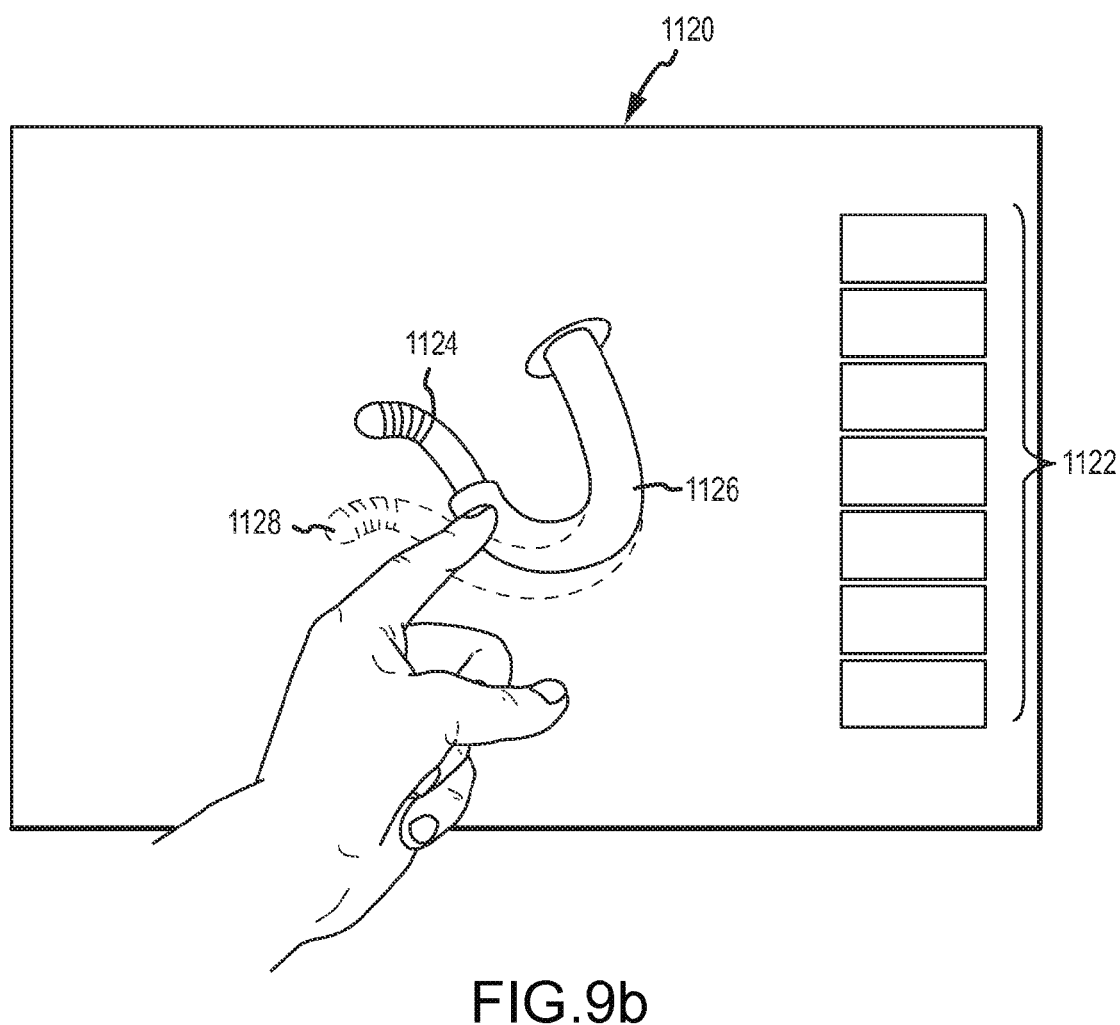

FIGS. 9a-9b are diagrammatic depictions of exemplary interface portions that may be provided by the user interface logic 226 for use with a touch-screen display. As will be described in more detail with respect to FIGS. 10a and 10b, the interface portions illustrated in FIGS. 9a-9b may be used individually (i.e., in isolation), or may be used in combination with each other and with other interface elements as part of a larger multi-user interface for a multi-user touch screen display.

FIG. 9a is a diagrammatic depiction of a first exemplary simplified interface portion, designated anatomical model interface portion 1100. The model interface portion 1100 includes a number of menu buttons 1102 and a view of an anatomical model 1104, which can represent a portion of a patient's anatomy (e.g., the patient's heart). The model view 1104 can be generated by the ECU 202 (for example, by executing display logic 234) based upon data received from the location data source 236 (e.g., the visualization, navigation, and mapping system 14). The ECU 202 (for example, by executing user interface logic 226) can then cause the model view 1104 to be displayed as part of the interface portion 1100 on a display, such as, for example, a touch screen display.

The model interface portion 1100 can be configured to receive user inputs with respect to the model view 1104 to direct execution of a variety of functions, including, for example only, manipulating model view 1104 and/or directing movement of a catheter or sheath by placing lesion markers, waypoints (i.e., to specify a pre-planned movement for the catheter), virtual sensors, or automated movement targets and lines on or within the anatomic model. The user can provide these inputs by directly interacting with the objects on the screen, such as the model view 1104 or the on-screen menus and/or on-screen buttons 1102. Interaction with a touch-screen interface portion is described in detail in PCT/US2011/30764, entitled "INTUITIVE USER INTERFACE CONTROL FOR REMOTE CATHETER NAVIGATION AND 3D MAPPING AND VISUALIZATION SYSTEM" and published as WO 2011/123669, hereby incorporated by reference in its entirety as though fully set forth herein. A brief description of interaction with a touch screen interface portion is set forth below.

Model manipulation can be performed via touch-based inputs made with respect to the model view 1104, the menu buttons 1102, or a combination. For example, one of the menu buttons 1102 may be used to select a particular view manipulation mode (e.g., rotate, pan), and touch-base input can be made in that mode. When in rotate mode, a user can rotate a 3D cardiac geometry 1104 by touching the screen with a finger and dragging across the screen to spin the 3D model about an axis orthogonal to both the surface normal of the screen and the direction of the dragging motion. When in pan mode, a dragging motion across the screen can move the model across the screen. The zoom can be controlled, for example, through a pinching (zoom out) or expanding motion (zoom in) of multiple fingers, or through the use of an on-screen slider. Alternatively, the model interface portion 1100 can be configured (i.e., through user interface logic 226) so that each model manipulation command has an assigned unique touch-based gesture.

The anatomical model interface portion 1100 can be used to direct the movement of a medical device in a variety of ways. First, the user can select target points 1106, 1108 within the model. These target points can be used to identify lesion points for intended or completed therapy delivery (shown as point 1108), waypoints for semi-automated step-wise catheter movement (shown as point 1106), destination points for fully automated movement, or as relative markers or virtual electrophysiology sensors that can have no impact on relative movement. In an embodiment, a target point 1106, 1108 can be initially set by tapping on the touch screen in a position where a target point is desired. If the user desires to move a target point, the user can for example, select it by tapping it, and then drag the point to a new location. Additionally, after selecting a point, the software can call up a list of menu options that can allow the user to configure or view one or more parameters of the point. Such parameters can include, for example, the nature of the point (e.g. marker, lesion point, waypoint, sensor) the distance of the point above the surface, or specific data recorded or computed at the point.

In addition to setting individual target points, the user can also specify a line or path 1110 along the surface of the model 1104 by touching and dragging a finger across the screen. Such a generated line can be similar to a splined series of waypoints. Furthermore, in an embodiment, the user can select a point along the line and "lift" that point away from the surface by, for example, using a slider or numerical input. Points adjacent to the selected point can additionally be lifted off as if they were tied to the selected point.

A user can also direct multiple motions for a medical device by setting multiple waypoints. For example, a user may select a medical device to move by tapping on a representation of the device, set a waypoint on a view of an anatomical model, rotate the view and move the original waypoint to, e.g., correct the position or depth of the waypoint, set another waypoint, and so on. After setting all desired waypoints, the user may initiate movement of the selected medical device to follow the path indicated by the waypoints.

FIG. 9b is a diagrammatic depiction of a second exemplary simplified interface portion, designated medical device interface portion 1120. The device interface portion 1120 includes a number of menu buttons 1122, a catheter representation 1124, and a sheath representation 1126. With the device interface portion 1120, a user can direct control of the catheter and/or sheath by entering a desired movement via one or more touch-based inputs.

The displayed catheter 1124 or sheath 1126 can be moved, for example, by first pressing on the image of the catheter or sheath to select it, followed by dragging the selected device in the direction of intended travel. Alternatively, the catheter 1124 or sheath 1126 can be selected by using a pinching motion as if the user is virtually grabbing the image. In an embodiment, while the user is dragging a virtual representation of the catheter or sheath, a ghost image 1128 of the current position of the device can be displayed as a reference. The ghost image 1128 can be based on real-time feedback of the actual catheter position as provided by a catheter positioning system such as ENSITE NAVX®. In an alternate embodiment, the ghost image 1128 can be the target position to which the virtual representation of the catheter or sheath is dragged. Once the user is satisfied with the movement, the user can release the selected catheter or sheath by removing his/her finger from the screen. The system can then be configured to then move the actual catheter in accordance with the user intended motion (subject to a safety switch), and can update the ghost image 1128 to reflect the actual movement. In another embodiment, the user can move a control point on the catheter or sheath and the actual catheter can be configured to track this point in real-time.

In another embodiment of device interface portion 1120, input on an "empty" area (i.e., a portion of the displayed interface without a displayed model view, menu, medical device representation, etc.) can be interpreted as though the user is looking down the longitudinal axis of the medical device (either from the proximal end to the distal end, or view-versa). In such an embodiment, a different set of input gestures may be used to direct the movement of the medical device. For example, a single-point touch-and-hold on the touch screen display may result in translational movement of the medical device, with the pressure of the input determining the speed of the translational movement. A drag to the left, right, or other direction on the touch screen may result in a corresponding curl of the device. A clockwise or counter-clockwise input on the touch screen may result in corresponding clockwise or counter-clockwise rotation or virtual rotation of the medical device. Such an embodiment of the device interface portion 11220 advantageously allows for touch-based inputs that mimic the motions and actions of a user manipulating a manual catheter handle.

The above-noted touch-based input methods can be used to perform a number of operations on one or more medical devices, such as translation, deflection, rotation, and relaxation (i.e., of one or more pull wires). Those operations can be directed by the control logic 228, which may issue commands to, e.g., translate one or more cartridges (such as cartridges 402, 404) or to actuate one or more pull wires via fingers 316, 318, 320 and 322.

In summary, the ECU 202, executing user interface logic 226, provides a physician, electrophysiologist, or other clinician with multiple different touch-based mechanisms for directing the movement of a robotically-controlled medical device. The user may enter target points (e.g., lesion markers, waypoints, virtual sensors, or automated movement targets and lines) on an anatomical model, directly interact with a displayed representation of the medical device, or enter input on the touch screen as though looking down the longitudinal axis of the medical device. These and other touch-based input mechanisms known in the art may also be combined with each other to provide a user or multiple users with multiple simultaneous input-entry options.

Figure 10A:
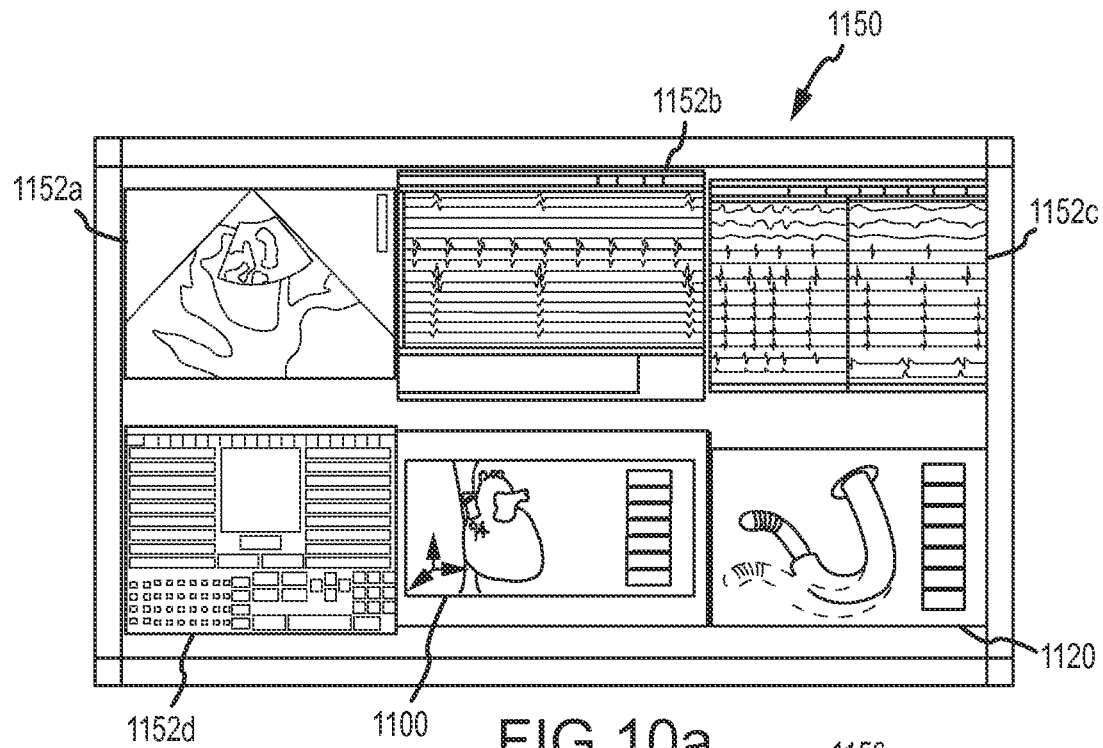
FIG. 10a is a view of a multi-user interface for use with a touch-sensitive input device in a robotic catheter system.
Figure 10B:
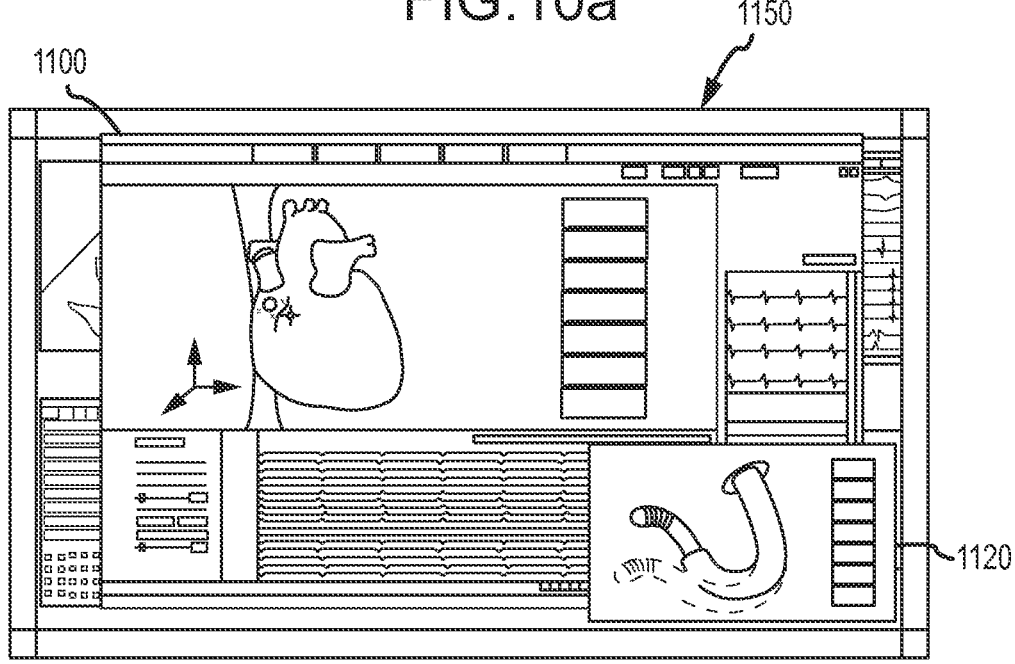
FIG. 10b is a view of the interface of FIG. 10a, showing enlarged interface portions.

FIGS. 10a-10b are diagrammatic depictions of an exemplary user interface configured for use by multiple users simultaneously, designated multi-user interface 1150. As noted in the Background, traditional input apparatus, including single-user touch screen displays, limit the actions available for a procedure and limit the speed and precision of those actions. The multi-user interface 1150 shown in FIGS. 10a-10b may increase the number of available user actions as well as increase the speed and precision of those actions.

The multi-user interface may find use, in particular, with a touch screen display that is capable of recognizing multiple inputs from multiple users simultaneously, such as a touch screen display available from Perceptive Pixel of New York, N.Y. Such a display, referred to herein as a multi-user touch screen display, may act both as the primary device in user input control system 100 as well as the primary display 12 for the system.

FIG. 10a illustrates a multi-user touch screen display displaying a multi-user interface 1150. The multi-user interface 1150 includes a number of interface portions 1100, 1120, 1152 separated on the display so that multiple users can interact with the multiple interface portions simultaneously. As shown, the multi-user interface includes a model interface portion 1100, a medical device interface portion 1120, and other interface portions 1152a, 1152b, 1152c. The device interface portion 1120 may be used to guide the movement of one or more robotically-controlled medical devices. The model interface portion 1100 may likewise be used to guide the movement of one or more medical devices through, e.g., target and waypoint selection. The model interface portion 1100 may also be used to manipulate the view of the model itself to better guide a medical device. The other interface portions 1152 may be used to display other information pertinent to the procedure, such as additional anatomical models or images, patient information such as ECG data, and system configuration information.

In an embodiment, it is desirable for a particular user or users to be able to manipulate a particular portion of the interface to the exclusion of other users. In particular, guidance of a medical device may be restricted to a particular user or user type, such as a physician or electrophysiologist. Such control restrictions can be created by associating each user input with a particular user or user type and interpreting user input according to the user or user type associated with the input and the permissions associated with that user or user type. As noted above, a user or user type can be associated with a particular input in a number of ways. First, the input itself can include biometric data that can be matched with user data saved in the system. Second, particular portions of the multi-user interface can be associated with particular users or user types.

Figure 11:
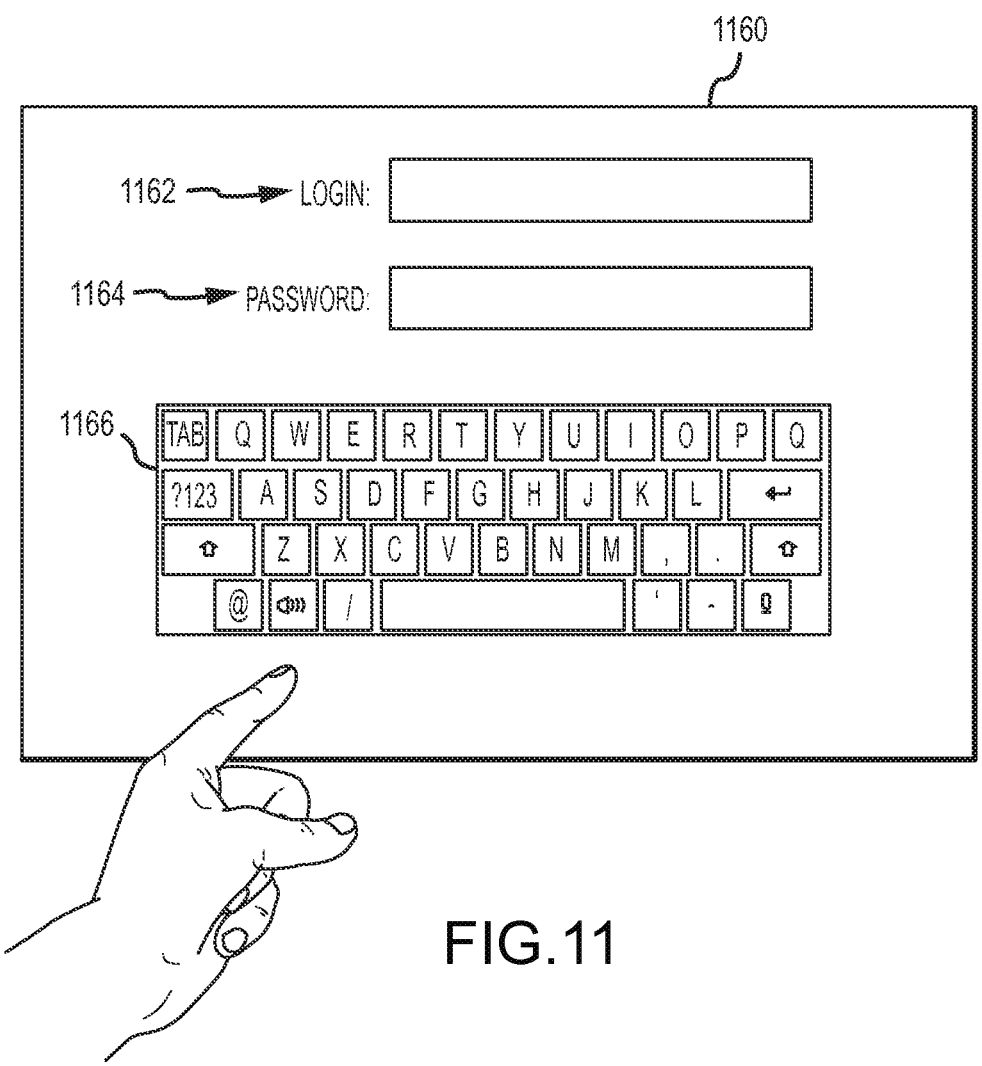
FIG. 11 is a view of a user login interface portion for use with a touch-sensitive input device.

One method for associating a particular portion of the interface with a particular user is through the creation of a "virtual touchpad" that allows a user to control a particular interface element such as, for example, medical device interface portion 1120, on a location of the touch screen interface of the user's choosing. To create a "virtual touchpad," a user, such as a physician, can make a pre-determined gesture or input at a desired location on the touch screen to prompt a login interface. In an embodiment, the pre-determined gesture is a circular motion on the touch screen, though other gestures or cues may be used. The login interface can be a typed PIN or password to be entered on the screen (i.e., as shown in FIG. 11), a verbal command (i.e., for voice recognition), or another identity verification mechanism. The identification information entered by the user can be cross-referenced against a stored set of users with permission to operate a virtual touchpad (i.e., permission to direct movement of a medical device in the patient). Once the user's identity is verified, and the user's permission to operate a virtual touchpad is confirmed, the virtual touchpad can be presented on the multi-user display at the location indicated by the user. In an embodiment, the virtual touchpad may be the medical device representation interface portion 1120 shown in FIG. 9b. The virtual touchpad may also be an empty input area in which the user can enter touch-based input as though looking along the longitudinal axis of a medical device. As long as the virtual touchpad is active, all inputs on the virtual touchpad may be associated with the user that logged in to initiate the virtual touchpad and interpreted accordingly.

FIG. 10b illustrates a multi-user touch screen display displaying the multi-user interface of FIG. 10a with interface portions 1100 and 1120 zoomed in. The multi-user interface 1150 can be actively modified by a user by enlarging and shrinking interface portions (such as portions 1100 and 1120, as shown), moving interface portions around the screen, and changing which interface elements are shown on the screen (i.e., a medical device representation, an anatomical model view, patient information, menu buttons, etc.). As a result, the multi-user interface 1150 can be actively tailored by the user to the resources available during a procedure, such as the number of users and the models and data available.

The multi-user interface 1150 illustrated in FIGS. 10a-10b advantageously allows for great input flexibility during a robotic procedure. A single user can control a single device or multiple devices. Multiple users can control multiple devices simultaneously. The same users or a different user or users can manipulate anatomical model views to provide the most appropriate views throughout a procedure. This flexibility allows for improved speed and precision over known interfaces and known input mechanisms.

FIG. 11 is a view of an exemplary user login interface 1160 that can be used to associate an interface portion with a particular user or user type. The login interface 1160 includes a user identification portion (i.e., a user name or login) 1162, a verification portion (i.e., a password) 1164, and a touch screen keyboard 1166 to enter identification and verification information. It should be understood that the login interface 1160 illustrated is exemplary in nature; many different types of identification and verification methods may be used, such as typed (as shown), biometric (e.g., fingerprint, retinal scan), verbal (i.e., for a spoken password or voice recognition), or other known methods.

To prevent unauthorized access to a virtual touchpad or another restricted-use portion of the multi-user interface, the portion of the interface associated with a particular user or user type may be dissociated from the user or user type upon a dissociation event. A dissociation event may be, but is not limited to, a dissociation input by the associated user (i.e., an explicit "logout"), the passage of time since the last input by the associated user, or the passage of time since the user was associated with the interface portion.

Figure 12:
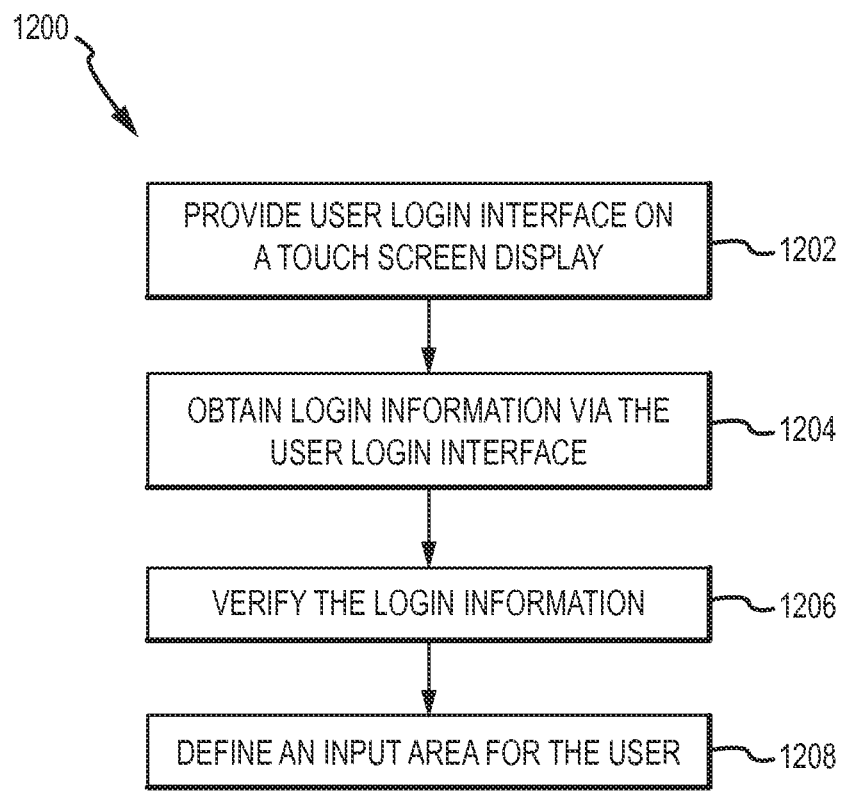
FIG. 12 is a flow chart illustrating a method of associating a user type with a portion of a multi-user interface for a touch screen display.

FIG. 12 is a flow chart illustrating a method 1200 of associating a portion of an interface with a user type. The method 1200 may be programmed into the user interface logic 226 for execution by the ECU 202 in a robotic catheter system including a multi-user touch screen display input device. It should be understood that the steps of method 1200 are exemplary only and that other methods of associating one or more inputs with a user or user type are contemplated.

The method 1200 begins with the step 1202 of providing a user login interface on a touch screen display. The user login interface can be in the form shown in FIG. 11 (i.e., a prompt to type in login information), or can be in some other form, such as a visual prompt to speak a login code or a prompt to enter biometric data, such as a fingerprint or retinal scan.

After the login interface is provided, the method 1200 continues with the step 1204 of obtaining login information via the user login interface. As noted above, this step is not limited to typed information. Login information can also be verbal, biometric, or in some other form. Login information can include, for example, an identification portion (i.e., a user name) and an identity verification portion (i.e., a password, PIN, or the like). In an embodiment, the identification portion and the identity verification portion can be the same information from the user, such as biometric data.

After the login information is obtained, the method 1200 continues with the step 1206 of verifying the login information to determine or confirm the user identity or user type of the user attempting to log in. The verification step may include a comparison of login information to a stored database of login information (i.e., stored user identity information matched with stored identity verification information).

After the user's identity and/or user type has been verified, the method continues with the step 1208 of defining an input area for the user. The defined input area may be a discrete portion of the user interface—i.e., a portion or window of the interface displayed on the multi-user touch screen display. The defined input area, also referred to as a "virtual touchpad," may be illustrated as such on the display (for example, with a discrete box, a line surrounding the defined area, a separate color for the defined area, etc.), or may blend in with the rest of the interface. The input area (and any input made within the input area) may be associated with the logged in user.

The method 1200 may be executed one or more times during a medical procedure. A physician may prompt the method by making a predefined gesture or input on the touch screen display (e.g., a circular gesture) or through some other input command, such as a voice command. The method may be executed by the ECU 202 to provide the physician with a virtual touchpad on a desired portion of the multi-user touch screen display. The method 1200 may be executed again if the physician wishes to move the virtual touchpad to a different location on the display. The physician may log out of the virtual touchpad and prompt the method 1200 from another location on the touch screen display. Additionally or alternatively, another physician or electrophysiologist may prompt a virtual touchpad at a different location on the display to control a different medical device, such that multiple users are interacting with the multi-user display to direct the movement of multiple different medical devices on different virtual touchpads. For example, the first physician may direct the movement of a sheath, and the second physician may direct the movement of a catheter disposed within the sheath, or the first physician may direct the movement of an ablation catheter, and the second physician may direct the movement of a separate mapping catheter.

Figure 13:
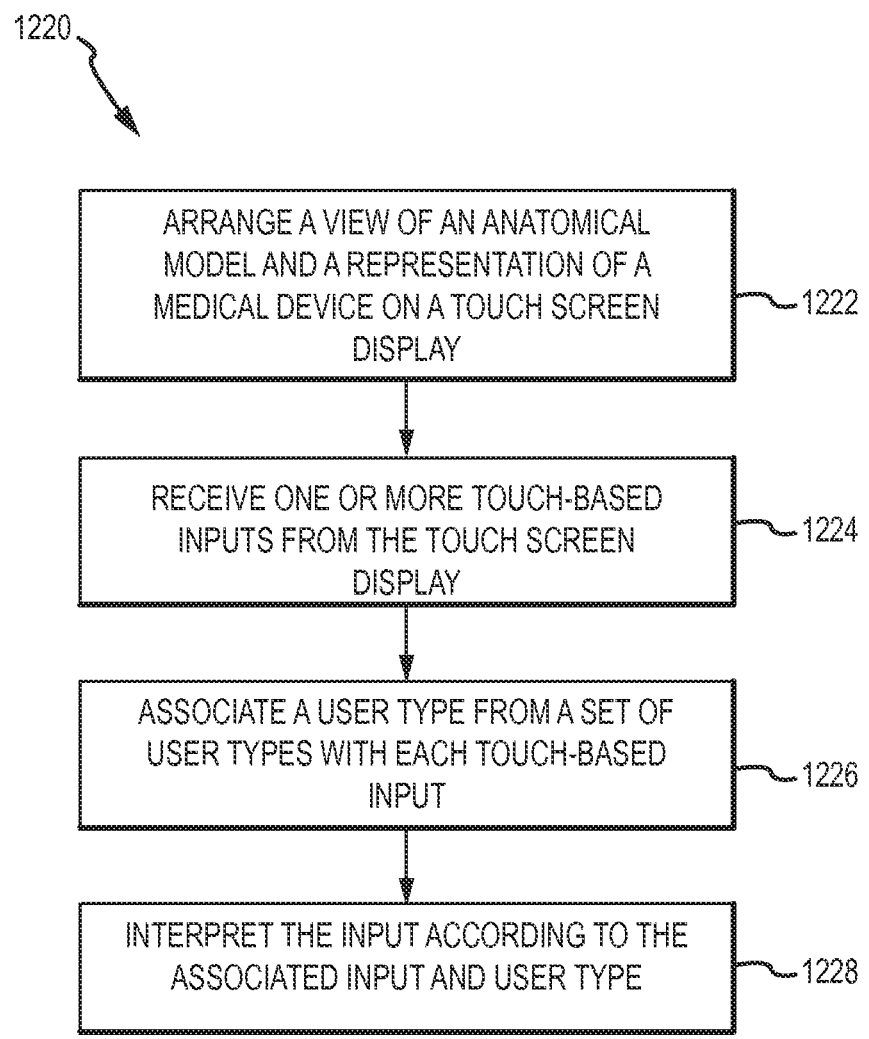
FIG. 13 is a flow chart illustrating a method of providing a multi-user interface for robotic catheter system.

FIG. 13 is a flow chart illustrating a method 1220 of providing a multi-user touch-based user interface for a medical device remote catheter guidance system. The method 1220 may be programmed into the user interface logic 226 for execution by the ECU 202 in a robotic catheter system including a multi-user touch screen display input device. It should be understood that the steps of method 1220 are exemplary only and that other methods of operating a user interface are contemplated.

The method 1220 begins with the step 1222 of arranging a view of a anatomical model and a representation of a medical device on a touch screen display, such as a multi-user touch screen display. More than one view of an anatomical model may be displayed, and displayed views may be of the same model (for example, orthogonal views) or different models (for example, a 3D model built from CT data and a separate 3D model built from MRI data). Similarly, more than one medical device may be displayed. For example, a coupled catheter and sheath may be displayed, or two separate catheters. The anatomical model and medical device representation may be arranged in different portions of an interface (i.e., as shown in FIGS. 10a-10b) or in the same portion of an interface (i.e., with the medical device representation superimposed on the model view).

In step 1222, a medical device representation may be arranged in an interface portion associated with a particular user or user type (i.e., a "virtual touchpad"). Similarly, a anatomical model view on which input can be made to direct movement of a catheter may be arranged in an interface portion associated with a particular user or user type. The interface portion may be associated with the user or user by executing the method 1200 illustrated in FIG. 12 or through some other method. In an embodiment, multiple different interface portions in which different model views and/or device representations may be associated with different users. One or more of the interface portions may be associated with only a single user or user type, and one or more of the other interface portions may be associated with multiple users or user types.

After one or more model views and one or more medical device representations are arranged on the touch screen display, the method continues to the step 1224 of receiving one or more touch-based inputs from the touch screen display on which the representation and model view are arranged. The touch-based inputs may be with respect to the model view, the medical device representation, or both. The input may be received as one or more gestures (each including, e.g., a location, gesture type, and direction) or as one or more points of raw input data (each including, e.g., a location and a touch pressure). The inputs may be processed in parallel (i.e., simultaneously) or in series.

After the one or more touch-based inputs are received from the touch screen display, the method continues with the step 1226 of associating a user type from a set of user types with each touch-based input. Input may be associated with a user type according to the location on the screen of the input—i.e., when the location of the input is within an interface portion already associated with a particular user or user type—or according to another piece of data. Other data that may be used to associate a user with an input includes biometric data (i.e., a fingerprint accompanying the input) or other identification data known in the art.

Once each input is associated with a user type, the method 1220 continues to the step 1228 of interpreting each input according to the associated input and user type. The interpretation step 1228 may include determining or confirming the permissions associated with the user type that is associated with the input. If the user type associated with the input has permission to direct the movement of a medical device, the input may be interpreted as a command to move a medical device with the RCGS 10 and the input may be passed on to control logic 228. If the user type associated with the input has permission to manipulate a view of an anatomical model, the input may be interpreted as an anatomical model manipulation command and the user interface logic 226 may query an updated model view from the display logic 234.

It should be understood that steps 1224, 1226, and 1228 are not intended to be limited to a particular processing scheme or order. Each input may be received, associated with a user type, and interpreted as the input is entered to the touch screen, or multiple inputs may be buffered for batch processing at any of the steps. In addition, the method may be configured (i.e., by configuring the user interface logic 226) to only accept a certain number of simultaneous inputs so that system processing does not slow the procedure or for another reason.

In an exemplary embodiment of the method 1220, a representation of a first catheter may be arranged in a first interface portion on a first location on the multi-user touch screen display, a representation of a second catheter may be arranged in a second interface portion on a second location on the multi-user touch screen display, and orthogonal views of an anatomical model may be arranged in a third interface portion on the multi-user touch screen display. The third interface portion may also include a representation of both catheters superimposed on the orthogonal views. The first catheter interface portion may be associated with a physician user type (a physician having logged in), the second catheter interface portion may be associated with an electrophysiologist user type (an electrophysiologist having logged in), and the model view may be associated with a user type without permission to direct the movement of a medical device.

The physician may direct the movement of the first catheter with reference to the representation in the first interface portion and by viewing the position, orientation, and shape of the first catheter with respect to the patient's anatomy by viewing the third interface portion. The electrophysiologist may similarly (and simultaneously) direct the movement of the second catheter with reference to the second interface portion. Significantly, a third user can manipulate the model views in the third interface portion to give the physician and electrophysiologist optimal views of the respective catheters with respect to the patient's anatomy. The physician and electrophysiologist may also directly manipulate the third interface portion by making touch-based input in the third interface portion. Of course, many other combinations of users and interface portions and arrangements are possible and contemplated.

Operating a multi-user interface on a multi-user touch screen display according to the method 1220 presents significant advantages. The interface can be scaled to the number of users to maximize the available personnel. For example, multiple users can simultaneously direct the movement of multiple medical devices (as described above), or a single user can simultaneously direct the movement of multiple medical devices, while one or more users can simultaneously manipulate one or more views of anatomical structures and of the guided medical devices. Portions of the interface can be associated with particular permissions (via user types) so that multiple views of the same medical device may be shown in the interface without the risk of multiple movement commands entered with respect to the different views. Because the interface can be scaled to safely accommodate multiple users, the efficiency and precision of a procedure involving a robotically-guided medical device can be improved.

Further configurations, such as balloon-based delivery configurations, can be incorporated into catheter embodiments consistent with the disclosure. Furthermore, various sensing structures can also be included in the catheter, such as temperature sensor(s), force sensors, various localization sensors (see description above), imaging sensors and the like.

As used herein "distal" refers to an end or portion thereof that is advanced to a region of interest within a body (e.g., in the case of a catheter) while "proximal" refers to the end or portion thereof that is opposite of the distal end, and which can be disposed outside of the body and manipulated, for example, automatically through the RCGS 10.

It should be understood that an electronic controller or ECU as described above for certain embodiments can include conventional processing apparatus known in the art, capable of executing pre-programmed instructions stored in an associated memory, all performing in accordance with the functionality described herein. To the extent that the methods described herein are embodied in software, the resulting software can be stored in an associated memory and can also constitute the means for performing such methods. Implementation of certain embodiments, where done so in software, would require no more than routine application of programming skills by one of ordinary skill in the art, in view of the foregoing enabling description. Such an electronic control unit or ECU can further be of the type having both ROM, RAM, a combination of non-volatile and volatile (modifiable) memory so that the software can be stored and yet allow storage and processing of dynamically produced data and/or signals.

It should be further understood that an article of manufacture in accordance with this disclosure includes a computer-readable storage medium having a computer program encoded thereon for implementing the multi-user display interface for an RCGS described herein. The computer program includes code to perform one or more of the methods disclosed herein.

Many different types of so-called "touch screens" can be utilized to perform a surgical operation according to this disclosure, including resistive-type (e.g., displays having several layers including two thin metallic and electrically conductive spaced-apart layers acting like a pair of voltage dividers), surface acoustic wave (SAW)-type (e.g., displays having ultrasonic waves passing over the display surface), capacitive-type (e.g., displays having an insulator and a transparent conductive coating such that when a conductor, such as a human hand, a magnet, or active metallic element, touches the screen it changes the capacitance at the site of contact) which include surface capacitance-type displays in which the conductive coating or layer has an electrical voltage imposed upon it and the conductor forms a dynamic capacitor upon contact. Capacitive-type displays also include projected capacitance-type (PCT) displays in which the conductive layer is etched to form a grid pattern or perpendicular patterns, thus creating a grid of discrete capacitive elements (the latter of which is particularly suited for multi-touch operation (s)). Other types of display technology usable according to this disclosure include strain gauge (also known as force panel technology, or FPT), in which the FPT display screen is spring-mounted and the gauges determine deflection when the screen is touched. One advantage of FPT is that the magnitude of force applied to the screen is measured (in the Z-axis) and thus can be used. An FPT or other display also can indirectly measure (or approximate) the magnitude of contact by a relatively malleable or deformable instrument (including a human digit) by measuring the rate of change of the contact surface or "patch" (e.g., from a relatively small area to a relatively larger or growing area and vice versa). Another touch screen type usable with the present disclosure is optical imaging, wherein two or more image sensors (e.g., two pairs of opposing cameras) are placed around the edges of a display screen and the display is backlit, such that contact appears as a shadow. Each pair of cameras triangulates the shadow to locate the position of the contact. Another technology is dispersive signal technology (DST) in which the mechanical energy imparted to a glass display screen is detected upon contact, but ongoing stationary contact is not detected. Thus, DST technology can be readily applied for dynamic or continuously-moving control of a catheter displayed upon a glass display screen. Yet another technology more recently introduced involves acoustic pulse recognition (APR) technology wherein two or more piezoelectric transducers translate mechanical energy of contact (vibration) into an electronic signal. As with DST, APR technology does not detect ongoing stationary contact.

Although a number of embodiments of this disclosure have been described above with a certain degree of particularity, those skilled in the art could make numerous alterations to the disclosed embodiments without departing from the spirit or scope of this disclosure. All directional references (e.g., upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of the disclosure. Joinder references (e.g., attached, coupled, connected, and the like) are to be construed broadly and can include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure can be made without departing from the disclosure as defined in the appended claims.

What is claimed is:

1. A control system, comprising:
   an electronic control unit;
   computer-readable storage coupled to the electronic control unit, the storage configured to store a set of user types, each of the user types corresponding to a respective user access permission;
   a user interface including one or more touch screen displays configured to receive user input, and configured to present a plurality of different display outputs from a plurality of sources of anatomical models on the one or more touch screen displays; and
   control logic configured to be executed by the electronic control unit, wherein the control logic is configured to identify the user access permission corresponding to the user type of the received user input, and to allow control of one or more of the plurality of different display outputs in accordance with the identified user access permission.

2. The control system of claim 1, wherein the user interface is configured to accept a received user type for a user, and wherein the electronic control unit is configured to store the user type and its respective user access permission in the computer-readable medium.

3. The control system of claim 1, wherein the user interface is configured to receive simultaneous inputs from at least two different users, and wherein the electronic control unit is configured to store the user types and their respective user access permissions in the computer-readable medium.

4. The control system of claim 3, wherein the control logic is configured to prioritize the user input for controlling one or more of the plurality of different display outputs for each of the at least two different users based on the respective user access permissions of the respective user types.

5. The control system of claim 3, Wherein the control logic is configured to allow control of at least one of the different display outputs by a first user having an associated one of the user access permissions of a higher level than the user access permission of a second user.

6. The control system of claim 3, wherein the control logic is configured to disallow control of the least one of the different display outputs by the second user where the first user is associated with the user access permission of a higher level than the user access permission of the second user.

7. The control system of claim 1, wherein said user interface receives the user input as one or more gestures.

8. The control system of claim 1, wherein at least one of the plurality of sources of anatomical models comprises an electrophysiology cardiac model, and wherein a respective one of the display outputs comprises a cardiac chamber geometry.

9. The control system of claim 1, wherein at least one of the plurality of sources of anatomical models comprises an intra-cardiac echo model, and wherein a respective one of the display outputs comprises an intra-cardiac echo image.

10. The control system of claim 1, Wherein at least one of the plurality of sources of anatomical models comprises an intra-fluoroscopy model and wherein a respective one of the display outputs comprises a real-time x-ray image.

11. The control system of claim 1, wherein at least one of the plurality of sources of anatomical models comprises a computed tomography model and wherein a respective one of the display outputs comprises a computed tomography image.

12. The control system of claim 1, wherein at least one of the plurality of sources of anatomical models comprises a magnetic resonance imaging model and wherein a respective one of the display outputs comprises a magnetic resonance imaging image.

13. The control system of claim 1, wherein the plurality of sources of anatomical models comprises a plurality of anatomical models selected from the group comprising electrophysiology cardiac models, intra-cardiac echo models, and fluoroscopy models.

14. The control system of claim 1, wherein the plurality of sources of anatomical models comprises a representation of data provided by an electrophysiology recording system.

15. A method for controlling user control of a multi-display monitor having a plurality of display segments, comprising:
    receiving, via a user input, a respective user type for a plurality of users;
    storing, in a storage medium, a user access permission for each of the user types;
    presenting a plurality of display outputs from a plurality of sources of anatomical models on the plurality of display segments; and
    using an electronic control unit, identifying the user access permission corresponding to the received user type, and permitting control of the plurality of display segments by the plurality of users based on the respective user access permissions of the users attempting to control the plurality of display segments.

16. The method of claim 15, further comprising the electronic control unit resolving simultaneous attempts by more than one of the plurality of users to control a common one of the display segments based on the relative user access permissions of the users attempting to control the plurality of display segments.

17. The method of claim 15, wherein the electronic control unit permits control of different ones of the plurality of display segments to each of the plurality of users attempting to control the plurality of display segments based on their respective user access permissions.

18. The method of claim 15, wherein the plurality of sources of anatomical models comprises a plurality of anatomical models selected from the group comprising electrophysiology cardiac models, intra-cardiac echo models, fluoroscopy models, computed tomography model, and magnetic resonance imaging models.

* * * * *